(12) United States Patent
Tomita

(10) Patent No.: US 7,351,536 B2
(45) Date of Patent: Apr. 1, 2008

(54) REVOLVER-2: A NOVEL TRANSPOSON-LIKE ELEMENT FROM RYE

(75) Inventor: Motonori Tomita, Tottori (JP)

(73) Assignee: Tottori University, Tottori (JP)

( * ) Notice: Subject to any disclaimer, the term of this patent is extended or adjusted under 35 U.S.C. 154(b) by 0 days.

(21) Appl. No.: 10/927,100

(22) Filed: Aug. 27, 2004

(65) Prior Publication Data

US 2005/0091710 A1    Apr. 28, 2005

(30) Foreign Application Priority Data

Aug. 29, 2003    (JP) .............................. 2003-307234

(51) Int. Cl.
 *C12Q 1/68* (2006.01)
 *C07H 21/04* (2006.01)
(52) U.S. Cl. ......................................... 435/6; 536/24.3
(58) Field of Classification Search ............... 536/23.1, 536/24.3, 24.1

See application file for complete search history.

(56) References Cited

U.S. PATENT DOCUMENTS 5,783,383 A * 7/1998 Kondo et al. ................... 435/5
6,306,636 B1 * 10/2001 Haselkorn et al. .......... 435/232

OTHER PUBLICATIONS

Kalendar R, Vicient CM, Peleg O, Anamthawat-Jonsson K, Bolshoy A, and Schulman AH. Large Retrotransposon Derivatives: Abundant, Conserved but Nonautonomous Retroelements of Barley and Related Genomes (2004) Genetics, vol. 166, pp. 1437-1450.*
Friebe et al. Identification of a complete set of isogenic wheat/rye D-genome substitution lines by means of Giemsa C-banding. (1988) Theor. Appl. Genet., vol. 76, pp. 473-479.*
Lukaszewski et al. Translocation and modifications of chromosomes in Triticale ×Wheat hybrids. (1983) Theor. Appl. Genet., vol. 64, pp. 239-248.*
Singh et al. Expressed sequence tags from cold-stressed winter rye seedlings. (2000) GenBank Accession BE704778, pp. 1-2.*
Yang et al. Kiddon, a new transposable element family closely associated with rice genes. (2001) Mol. Genet. Genomics, vol. 266, pp. 417-424.*
Database EMBL 'Online', Sep. 7, 1999, "Secale cereale clone F17 hypervariable DNA sequence," XP002307696 retrieved from EBI accession No. EM_PRO:AF175285, Database accession No. AF175285.
Database EMBL, Mar. 5, 1999, "*Hordeum vulgare* insertion sequence in a copia-like retroelement BARE-1, gypsy-type retrotransposon BARE-100 DNA, solo-LTR sequence," XP002307697 retrieved from EBI Database accession No. AB014756.
Manninen et al., "BARE-1, a copia-like retroelement in barley (*Hordeum vulgare* L.)," *Plant Molecular Biology*, 1993, pp. 829-846, vol. 22, No. 5, Kluwer Academic Publishers, Belgium.

Rogowsky et al., "Structural heterogeneity in the R173 family of rye-specific repetitive DNA sequences," *Plant Molecular Biology*, 1992, pp. 95-102, vol. 20, No. 1, Kluwer Academic Publishers, Belgium.
Balcells et al., "Transposons as tools for the isolation of plant genes," *Trends in Biotechnology*, Jan. 1991, pp. 31-37, vol. 9, No. 1, Elsevier Publications, Cambridge, GB.
Database EMBL 'Online', Jan. 3, 2003, "*Hordeum vulgare* clone HmaLTR-INS Sukkula retrotransposon long terminal repeat, complete sequence" XP002314849 retrieved from EBI accession No. EM_PRO:AY054378.
Kalendar Ruslan et al: "Large retrotransposon derivatives: Abundant, conserved but nonautonomous retroelements of barley and related genomes" *Genetics*, vol. 166, No. 3, Mar. 2004, pp. 1437-1450, XP002314846 ISSN: 0016-6731.
Database EMBL 'Online', Jan. 3, 2003, "*Hordeum vulgare* Sukkula retrotransposon long terminal repeat, partial and complete sequences", XP002314850 retrieved from EBI accession No. EM_PRO:AY054376.
Database EMBL 'Online', Nov. 9, 1999, "nbxb0048A01r CUGI Rice BAC Library Oryza sativa genomic clone nbxb0048A01r, genomic survey sequence" XP002314851 retrieved from EBI accession No. EM_PRO:AQ853983.
Database EMBL 'Online', Aug. 7, 2001, "Triticum monococcum actin (ACT-1) gene, partial cds; putative chromosome condensation factor (CCF), putative resistance protein (RGA-2), putative resistance protein (RGA2) and putative nodulin-like-like protein (NLL) gene, complete cds; and retrotransposons Josephine, Angela-2, Angela-4, Heidi, Gret" XP002314847 retrieved from EBI accession No. EM_PRO:AF326781.
Database EMBL 'Online' Sep. 14, 2000 "Sc01_01g02)R Sc01_AAFC_ECORC_cold_stressed_winter_rye_seedlings Secale cereale cDNA clone Sc01_01g02, mRNA sequence" XP002314848 retrieved from EBI accession No. EM_PRO:BE704778.
Tomita et al., "The dispersed repeated DNA sequence SacI family being transcribed in rye," *Japanese Breeding Magazine*, 1996, p. 57, Japanese Society of Breeding (including English language translation).
Chen et al., "MATS: A Rapid and Efficient Method for the Development of Microsatellite Markers from YACs," *Genomics*, 1995, vol. 25, pp. 1-8, Academic Press, Inc., San Diego, CA, U.S.

(Continued)

*Primary Examiner*—Cynthia Collins
*Assistant Examiner*—Cathy Kingdon Worley
(74) *Attorney, Agent, or Firm*—Buchanan Ingersoll & Rooney PC

(57) ABSTRACT

The object of the present invention is to obtain a novel transposon-like element specifically present in the genome of rye and the like. According to the present invention, a DNA sequence of a transposon-like element Revolver comprising 3,041 nucleotide pairs, and DNA sequences of structural mutants thereof were provided. The DNA sequence of the transposon-like element Revolver, the DNA sequences of genes having transcriptional activity encoded by Revolver, and the DNA sequences of structural mutants thereof can be utilized for detection of a genome, development of DNA markers, identification of chromosomes, a probe for study on evolution, an entry point of PCR and the like, in useful resource plants of Poaceae.

8 Claims, 4 Drawing Sheets

OTHER PUBLICATIONS

Hehl, "Transposon tagging in heterologous host plants," *TIG*, 1994, vol. 10, No. 11, Elsevier Science Ltd., London, England.

Hisako, *Japan Journal of Genet.*, 1987, vol. 61, pp. 75-100.

Tomita et al., "cDNA structure of the 2.5kb repetitive gene family in the rye genome," *Breeding Research* (*Ikushugaku Kenkyu*, 1999, vol. 1, Supplement 2, p. 6 (with English language translation).

Tomita et al., "Chromosomal Localization of the 2.8kb Multigene Family of Rye," *Genes Genet. Syst.*, 2000, vol. 75, p. 372 (Abstract).

Tomita et al., "Transcription and splicing of the 2.5kbp-repetitive sequence family interspersed in the genome of rye, *Secale cereale*," *Preprint and Program of the 21st Annual Meeting of the Molecular Biology Society of Japan*, 1988, p. 238,, 1P-046.

* cited by examiner

Southern blotting

1. S. cereale (RR)
2. S. montanum (RR)
3. S. fragule (RR)
4. S. silvestre (RR)
5. T. aestivum (AABBDD)
6. T. monococcum (AA)
7. T. durum (AABB)
8. T. polonicum (AABB)
9. T. tauschii (DD)
10. Dasypyrum villosum (VV)
11. Hordeum bulbosum (HH)
12. Oryza sativa

```
                        SEQUENCE LISTING

<160> NUMBER OF SEQ ID NOS: 28

<210> SEQ ID NO 1
<211> LENGTH: 4000
<212> TYPE: DNA
<213> ORGANISM: Secale cereale

<400> SEQUENCE: 1
tccatctaat tcatcgcagg ccttgaatct tattcttttc atctttcact tctcatcctt      60
ttgtttaccg gagttcttca ttgtggttca tcatatttta attcatcctc gaaggtcttc     120
atcaagattc ttgttggagc tattgtttca tgtctttcaa ccttcaaggt tctcataatg     180
ctccttgttc ctccttttta ccggagtgct cttaacttcg ttcatctccg ttgcattctt     240
ctttcacttg tttaactctc aaggttcctt ggtttcactc gtctgtcaaa gaagcaactt     300
```

```
tgttttacct cttcctcttc cgttttacc ggagatatct ctaggatctc gggtcgagat      360
cctctgttag tgtgggagag ttgtgacgcc cgagaccgac gtccagaaga ttccagaagg      420
ttcaagaaga ttccagatgt tccgggttgc cgtgtgttct ttgtgcttgt gttatttatt      480
tattttgcat gcatcatgtc atcatgccat catgtcatat tttattttgc atctcaacct      540
aaataaaccg tggtgccttc ggtccattta atcgaggga aggtgacttc tctttataac      600
atataaaagc ctctcaatat tagggagcta aatgttttag tttgcacttc ctttgtgttg      660
gaactatttt tgttgggttg gtaatatccc gtaaagcctt ataaaaatgt tccatatttt      720
attctccgtt ctttgcctct tttctttta ttttgctctc tctcttttat ttctgtttaa      780
gaaataataa gaagagcagc agcagtttta aaaataatcc agcaggcctg aggccatctg      840
ggcttcaacc tcctctcctc ctccctcttt tggcccatct tccatctacg gccgtgtaac      900
tacttcctct acttccacta cgtccctcga cgacttgatt cgcccgaacg ggagtttcga      960
aggtataacc ccgtcgatga cccgtgtgat gtatgcttgt tgtgttgtat gaaatgtctc     1020
ccgtgtgtgc tccgtgtccg tttcgtccct tttgttgtcc tcggttgcct cgtcaccgac     1080
tcgtgggaac ccggtgacgg gatccaccca cttccatctt gttcgacttg ctcacgtcga     1140
ttctatcttt tgcaccggtc cctcaccgag ttaccggtac cgatatgttg tgtggcatca     1200
ttttcggaat cgttgccgtg gcacccctt ctttccacca cggtgacaaa tgcttcttat      1260
cttgttaatt gtcaaccttt taataaaact tgcataaact tgatcatgtc atccgcatca     1320
tgtaacaaca ttatggtatg taatttgttg tttgcttata attattaaac atgctcatgg     1380
ggttttccgg atatgttgtg tatttccggc ctcatttaaa atgtctagat attgtagttt     1440
tattatgctt cacctcttgc catgttaaaa ccctttaat cttgtcttgt aaataacgag      1500
agtcaactaa ataagtaata tgtggtgttt cgtcagtatg taactcgttg catattgagc     1560
tccacttaac ttgtagtttt tgtttgtgca ctttgccatg ccatgcataa ttaaaccgga     1620
catgcatcat acttggatgt gcatcgtatg ccatgttttt gcttgtgtgt ttaccgtgtt     1680 gtttgttct ttccggtttg cttctcttga tacttcggtt tcgttccgga gttgtgaggt      1740
ttctctcgtc agtgttgctc cgtcttcttg gatccgttct tctccctcgt ggaatcccag     1800
gcaagatgac cgaacccgga taccattact atctttgcct attgctagag tatcgctcta     1860
tagttttgcc tcgatgccca tgtctttctt gtcagcctcc tacttgtaac caattgccat     1920
gtttaaccaa cctacctatg caaaccgttg cttggctaag tacgcatcgc tcagccctct     1980
tatagcactg ttagttgcag gtgaagattg aagatgctta cttcatgttg aagtttggtt     2040
gggttatatc acactatata aatgcttaaa tgaaatcatc tatatactgg cagggtggaa     2100
ggctaagcct ttgcttggt gttttgttcc actcatgccg ttaggatccg tataagccgg      2160
tattatgttc cttgattatg cgtcctaaca cggttggggt gtatggaccc ccttgataaa     2220
ccgctaagtg ctaagtcttt tccatcaagt cccaacattt ggtactattt tcctcataat     2280
aacaacttaa ttaattaatt aaaattgcat agggggtcgc gtccccgagg attcttaatt     2340
ccacatagca gggggggcc cagcgctgat ggtgttggtc ccaaacgggg agactgcagg      2400
gccgccttgg ggcaacccga ggtatctggt atacctgtag aatcgccatc cggtcgtgtc     2460
tgagacctag atacgcgcgg ctactatcag ggtgtcgaca cgccgggagg atttgctgga     2520
ttagccttac cttagttcgg tttaacttga gcgggattcc gagaatactc gggtcttccc     2580
acctatggag ttgcgacttc gcggatcgtg ggcttgtgat ggccaagttg gaacaccctg     2640
cagggtttga acttcgaaag ccgtgcccgc ggttatgtgg cagatgggag cttgttaatt     2700
```

```
ccggttgtag ataacttgac acaatgtttc aatacactac cagcgtgtgt accgtgactg    2760
tcaatttccg aatagggatt cgggagttga acacggtggg gttatgtttg accggcttta    2820
gttaggatca cttcgtgatc atctttcgac cgatgctctt ctcttctcgg tctcttacg     2880 gaagtagtgc tagttgctgc tgcaggctct ttcttgttgt tccctcacct catattcttt    2940
cttcagcctt atcctcacct aaggcttaaa tagtcttgtt acccgggaac gggattgctg    3000
agtcctctgt ggctcacagt tacttcaccc acaccagttg caggttcagc cgagtttgat    3060
gcagggagct ggttcagtgc ttcaccagga gttcgatgaa gagtttgacc gtttgcttgt    3120
gacgtttcga tgttcagtag tggtttctac taggattcga tcctgacctg tggctttatg    3180 ttgtttggt atctttcttt ggatcttcac ccgtagtcgg gttgtgatgt tttgtatgat     3240 gattgcttt gtattgtatt gtgtgaagtg gcgagtgtaa gccaactatc tcttttgcaa     3300
tttaatccct cttttacatg agtcgtgcaa agataccaaa cttgagatca ttctaggatg    3360
ggcttatatc tttaagtcgt gcctcgacac gtaggagata tagtcccatc ctgggcatta    3420
catcggatcc tcgtagtgt attgttgtgg tgattagagg actcgtgttc gaataacatc     3480
ttgcaatccg ttgagagttg tagtataggt tagccaagag tctaagccgg cttctgcta    3540 tgaactccac tacccctt gataatgttg catgtatgat aggttctgtg gtaagacttg      3600
ctgagtacct ttgtactcat gtttgcttaa taactgttgc agaggagaac cctgcctg      3660 ctgatgggtt ctacatagac ggtgacggcg acgagtagct tgacaccaga cggagatctg    3720
gagcttgtga agggccttgt agatagtcag gctacaccaa gcctgtttta ttttctaagt    3780
tgtctgtact cagacatgta gctttcgctt gtgcttgtat gactgtatga cttgagtgtt    3840
ggtcatgtga ccccaacctg tatggatatg ttatgtatgg ctcttggagc ctcttaaata    3900
aagtactttg aatcatagag ttctgttgtg atgcaatgtt gtatttgcac atattgagca    3960
tattgcgtgt atgattgaaa tgcttggtat ctgtggatcc                          4000

<210> SEQ ID NO 2
<211> LENGTH: 3528
<212> TYPE: DNA
<213> ORGANISM: Secale cereale

<400> SEQUENCE: 2
atcgccccgc acaaagcctt tcggccttcc tctcaggcgg ccagaagcc ccgtgcgcca      60 tggccgctgc gccctccagc gcgccaaggc cgagcctcgg tggcgccgct tcgtttcctg    120
ctgcctcctc tactgcctca agccgagacc gctactgctg tgttatgttt gtgtgctgtt    180
gttttttttt gttttgtcaa gtgcagcgca ggcaagatcc ggtctccgaa tgtcatgaac    240
cactacttcc tccactacac gacgacccga caagttccac gaccgagtac cctctgatgc    300
aagtaccact acagtcgcga gaacgagaac cctcaagtac cacgacgacc gactcggcaa    360 gtaccctac ggaacgtgtt ctactaccgt cgcccggaaa agacggatgc gccaagtaca    420
tctacgaacg agttcgtcta ccgtcgccgt gtaccctac cgatgcgcca agtaccacta     480
cgcaagaacc gaacatctac cgatgccaag taccacgacc aagtaccacg acgaccacgt    540
gtacaactac gatgccgaga ccactacctt ttgacaagta ccactacgct cgacgactcg    600
aacatctaca aaacgacctc gtgaacaact accgtctcgg agacgcacca agtaccacta    660
catacgtgaa cgactaccgt cacctcgaag atgttgggtt catcaagtcc ctctccgaaa    720
cgaacgtgta ccactacttc cgctaccgtc gcccgagtac aactaccgcc tcgagaacga    780
```

```
ctacttcctc ttcttccagt acatccctcg acgactcgat tccgccccga aacaattgtt      840
tcgaaggtat aaccccgaga cgtgaccgtg tgatgcttgc ttgtggttgt atgaatgttc      900
ccgtgtgtca ccgtgccgtt tcgtccgttt gacatgttct cggttgcctc gtcaccgacc      960
cgtgggaacc ggtgacggga tcgccccacc tttcatctcg tttgactcat ccacggcatc     1020
tatcttttgc accggtctct caacgagtca ccggaaccga tatgacgcgt tgcatcattt     1080
tcggatcgtt gccgtgcacc ttttctttcc accacggcga caaatgcttc atatcttcat     1140
gtcaacccct tttaataaac cttgcattaa cttgatcatg tcatccgcat catgttaaca     1200
acactaaaaa tgttaattgt tgtttgcgta taattattaa acatgctcat ggggattttc     1260
cggatatgtt gttgttattt tcggcctcat ttaaaatgtc taaatagtgt agtttttatta    1320
tgcttcacct cttgccatgt taaaaacatt taatcttgtc ttgataaata atgagagtca     1380
actaaataat taaatgtggt gtttcgtcaa tatgcaattc gttgcatatt gagctccact     1440
taacttgtag tgttgtttgt gcattttgcc atgccatgca taattaaacc ggacatgcat     1500
catacttgga tgtgcatcgt atgccatgtt tatgattgtg tgtttaccga gttgtttgtt     1560
ttctttccgg ttgcttctcg tgttagcttc ggtttcgttc cggagttgtg aggattcgct     1620
cgactgttgc tccgtcttct tcttggatcc gttcttcttc ccttgtggaa tacaggcaag     1680
atgaccgaac ccgataccat tactatcttt gcctattgct agaagtctcg atctataggt     1740
ttgcctcgat gcccatgatc tcttgtcagc ctcctacttg taccaattgc catgtttaac     1800
caacctacct atgaaaaacct ttgaatggct agtacgttcg ctcagcccct cttatagctt    1860
tgttagttgc aggtgaagat tgaagattct tgcttcatgt tgaagtttgg ttgggttata     1920
tcacactata taaatgctta aaatgaaatc atctatatac tggctagggt gggaggctaa     1980
gcctttttgct tggtgtttgt tccactcatg ccgttaggat ccgtataaac cggtgttatg    2040
ttccttgatt atgcgttcct aacacggttg gggtgtatgg gacccctgaa taaaccgcta    2100
agtgctaagt actttccagc aagtcccaac attggtacta tttgactcat aataacaact    2160
taattaatta attgcatagg ggcgctcccg agatcctaat tctacatatg gggccagtct    2220
gatggtgttg gtcccaaacg ggaagtctgc ggaaccacca cgggaaacct cgagattggg    2280
tcctgtagaa tcgcccatcc ggtcgtgtcc tgagacttag atacgcgcgg ctactatcag    2340
ggtgtcgaca cgccgggggg atttgctgga ttagccttac cttagttcgg tttaacttga    2400
gcacgggatt ccgagaatac ttgggtcttc ccacctatgg agttgcgact ccgcggaacg    2460
tgggcttgta atgggtcaag ttggaacacc cctgcagggt ttgaactttc gaaagccatg    2520
cccgcggtta tgtggcagat gggagcttgt taatatccgg ttgtagataa cttgacacaa    2580
tgttctaata cactaccagc gtgtgtaccg tgactgtcaa tttctgaata gggattcggg    2640
agttgaacac ggtgggggtt atgtttgacc ggctttagtt aggatcactt cgtgatcatc    2700
tctcgaccga ggcacttctc ttctcgttct ctattacgta agtagtgcta ggccgctgct    2760
tgcagactct tgttgttcct tcacctcttt attctttttcg tcagccttat cctctcccaa    2820
ggcttaaata gtcttgttac ccgggaaacg ggattgctag aagttctctg tggctcacgg    2880
ttacttcacc acaccagtag caggttcagc cgagtttgat gcagaagatg gatcagaact    2940
ccaccgggag gacctgcagg catgcaagag ctcgttgaag agcgtggccg tagttgtgac    3000
gtttcgatgt tcagtagtgg tttctactag gattcgttcc tgacctatgg ctttatgttg    3060
ttttggtatc tttctttggg atcttcgccc gtagtcgggt tgtgatgttt tgaatgatgt    3120
tttgcttatg taatgtattt tgtgaagtgg ccgatgtaag ccaactatct tcttttgcaa    3180
```

```
tttaatccct cttttacatg agtcatgcaa agataccaaa ctttgggatc attctaggat    3240
ggggcttata ttctttaagt cgtgcctccg acagtaggag atatagtccc atcctgggca    3300
ttacaagttg gtattcagag ccttctccga cctagaagcc ccccactgat tgatcgaatc    3360
gttgacggtt gagtctaggc acacactaaa atatttcgag tcctatatta tatcggacga    3420
gtaggatttc tttgcttctc atcccccttt ctctctggtg aggactcctg acgactactc    3480
ttgtctctcc tattttcaaa aattgcacca attttctttt taggatcc               3528

<210> SEQ ID NO 3
<211> LENGTH: 4479
<212> TYPE: DNA
<213> ORGANISM: Secale cereale

<400> SEQUENCE: 3
gtagtcgtca ggagtcctca ccatgataaa gggatgagga gttgtgacgc ccgaagaccg     60
acgtcccaga agatcccaga agattcccga agattcccga agttccagat gttccgggtc    120
ctcccgtgtg tttcttttgt gcttgcgtta ttatttgct ttgcatcatg tcatcatgtg    180
catttcatca acatgttttc aaaacttgca tttgttcggg ctcccagttc tctccgttgt    240
ccgttctgag tccagtcaca ctcgcacgcg cccgtggcac ctccgaatat ttattttata    300
ggtggccgaa gaatgttctc ggaacgggtg gagacttggc gtgtggtctt attatagtgt    360
agacagcccg cctgccaaat tcatcgcgt tcggagttcg tttgatagcc caaccgttaa    420
acttatagcg gcactatagc cagataaacg tcggacgttt cagtgctctg aaacctgttg    480
ccgggttgcc atctctctct ctcttctcag cctacacatt ctacacaggc cacttttcat    540
ctcctcacta cttgtccgaa actgcccga accgacccgg ggttctcgtt accgttgggt    600
ccggatcttc cccaaacatc tcttaaatat ctccgttttc ttatttggac gccctacctt    660
ttttatctcg gccgttcgat tttgatcgga gggaccgaat agcccctaag ttaaacccac    720
ctactatata tagacaccta accctaaatt ttacgatcaa tgtcccatcc tcctcgttgc    780
cgccgaccat ccactgtccc tcgcatcctc gggatccatc ccgatctaca gagcccttt    840 cctcgttttc caaatctagc caaccagagc acctgccccc tccaccctcc tcgagcctga    900
ggcaggctcc tctgccccgg gcatccctc tcctccgttc ctgtcgctgc cagcgaggag    960
ccggaactcg ccggagcatc caagcgtcat cggaggacca cctcacccct tgatgtacgc   1020
catggccgcc gcccatggag tctccaccggt ccggctccag acgagtcctc cgccccggat   1080
ctggtactgc agcgtcctgg acctcacctg cagctacgtc gccccgtcga gttcctggag   1140
ctgtccttgt ccgctggtgc tccctgcacc gccggcaact gagcccccacg cgaacgtgtt   1200 agcatccgcc aaagggcctg cccatcgtgc gcccgcgcaa ggagacgagc gctctccttc   1260 tcgagccgcgt atggtgggct caagccgcat cgtgcgtccc tttcctctgg ccgcctccct   1320
ctggcccgag cagagcttcg cctcccgacg ttctgctgcc tcataccgtg ccggcgagca   1380
cgacgccgaa gcaccgcagt cgccgtgcct ctgcccatcc ttctcctgct ctcgttcctt   1440
ccaggctatc tccctcctct aatttctctc tctctatata tgcccaggag cagccaccgt   1500
gtcaccagat ctcactgccc gagcttcgga tatgtccatc ctcgccgttt tccacctcac   1560
ggcgccgccc cgtgccctgc tggccgtggc aaaagcagca tcgccgcacc agaaccctag   1620
gttcccagcc atggcacaa agcaagctat ctccgtttca gtttcagttt catcaggtaa   1680
gtgacagggt ccggttcatg tagcgtataa aggcattatg tatcaaactg gcatcgtagt   1740
```

```
cgactggtca cctgtgcatg cctccatcta ggagagctcg aggttcgagt cccagcttca   1800
catattttgc ttggccgtct tatccctttg tcatccggtc tgggcctgtt tctcagattc   1860
agcccgtgcc atgttttttt tcctagacga atttagctct tttccatgac ttgcatattt   1920
acagaaaatg ccatcttttc aaatgctgat aactctcaaa tcatgcgtca gttttttaaac  1980 aaacttgata tgttttttggc tcagaattt gcatagatta agaatgtcca actttcatcc   2040
ctgtttgaaa tgtttaactt gctcttttca ttaatttgtg taattaactt gctaaaatga   2100
tttatttcat aactaaataa ccgtagctcg gtttttaata aactttatat gtaaatgggg   2160
tagaaaatgt gtagaataac atgatgcact ttgttttgct gtttaacaac tttaaaatgt   2220
ggtaataggc agatcagtac caaattcata aatatgcaca tgaggagtta cggatatgtt   2280
gttggtattt ccggcctcat ttaaaacgtc taaataggta gtttattttt gctttcacct   2340
tctgccatgt ttaacaaaca attaactctt ttcttgtaaa taaacgagag tcaattaaat   2400
aattaatgtg gcgtttcgtc aatatgcaac ctcgttgcca tattgagctc cacttaactt   2460
gtagttttgt ttgtgcactt tgccatgcca tgcataatat aaccgaacat gcatcagctt   2520
ggatgtgcat cgtatgccat gcttatgctt gtgtgttacc atgttgcttg tttctttccg   2580
gttgcttctc ttgttagctt cggtttcgtt cccggagttg tgaggattcg ctcgactgtt   2640
gctccgtcta cttcgtggat ccgttcttct cccttgtgga atcccaggca agatgatcga   2700
acccggatac cattactatc tttgcctatt gctagtagtt ccgctctata gttttgcctc   2760
aatgcccatg tctttcctgt caacctccta cttgtaacca ttgccctgtt taaccaccct   2820
aactacgcaa acccttgctt ggctaaggtt actcgctcag cccttcttat agcattgtta   2880
gttgcaggtg aagattgaag atgcttgctt catgttgaag tttggttggg ttatatcaca   2940
ctatataaat gcttaaaaat gaaatcatct atatactggc agggtggaag ctaagccttt   3000
tgcttggtgt tttgttccac tcatgccgtt aggaaccgta taaaacggtg ttatgttcct   3060
tgattttgcg ttcctaacac ggttggggtg tatgggaccc ccttgataaa ccgctaagtg   3120
ctaagtcttt ttcagcaagt cccaacattt ggtactattt gcctcataat aacaacttaa   3180
ttaattaact taatgtggca ttaggggtc gcgtccccga ggattcttaa ttctacatag   3240
caggggggcc agtgctgatg gcgttggtcc caaacgggag tctgcagggc cgcttgggca   3300
acccgagtat ctgtatacct ctagaatccc atccggtcgt gtcctgagac ttagatacgc   3360
gcgcctacta tcagggtgtc gacacgccgg gaggatttgc tggattagcc ttaccttagt   3420
tcggtttaac ttgagcacgg gattccgaga atactcgggt cttcccacct atggagttgc   3480
gacttcgcgg atcgtgggct tgtgatgggc caagttggaa caccctgcag ggtttgaact   3540
ttcgaaagcc gtgcccgcgg ttatgtgtgca gatgggagct tgttaatatc cggttgtaga   3600
aaacttgact tttttttttg gggggactac ctgcgtgtat accgtgactg tcaatttccg   3660
aatgcgcgat tcggaagttg aacacggtgg ggttatgttt gaccggcttt agctaggatc   3720
ttcgtgatca tctttcgacc gatgcacttc tcttctcgct ctctattgcg taagttagtg   3780
ctagttgctg ttgcagactc ttgttgttcc ttcacctctc gttctttctt cagccttgtc   3840
ctcacccaag gcttaaatag tcttgttacc tgggaacggg attgctgagt cctctgtggc   3900
tcacagttac ttcaccacac cagatacagg ttcagccgag tttgatgcag gagctggttc   3960
aagtacttca tcgggagctc gatgaagagt ttcgcctgtt tgtttgtgac gcttcgacga   4020
tcagtagtgg tttctactag gattcgatcc tgacctgtgg ctgtatgttg ttttgtatgc   4080
gtcttttgga tcttcacccg tagtcgggtt gtgatgtttt gaatgatgta ttgcttatgt   4140
```

```
attgtattgt gtgaagtcgc gagtgtaagc caactatctc cttttgcatt ttaatccctc    4200
tttttacatg agtcgtgcaa agataccaaa cttgagatca ttctaggatg ggcttatatc    4260
tttaagtcgt gcctcgacac gtaggattat tgtcccttcc tgggcattac aaggttggta    4320
tcagagcctt ctccgaccta aagcccccca ctgattgatc gaatcgttga tggttgagtc    4380
taggcacaca ctgaaaacat tttgagtcct atattatatc ggagagtagg atttctttgc    4440
ttcttatccc ctttcttggt gaggactcct gacgactac                           4479

<210> SEQ ID NO 4
<211> LENGTH: 3413
<212> TYPE: DNA
<213> ORGANISM: Secale cereale

<400> SEQUENCE: 4
gtagtcgtca ggagtcctca ccacgatgaa ggggatgagg agtaaaagaa accctactct      60
ccgatatata cataggactc gaaacatttt gtaatgcccc ggatgtaaca ctttccccct     120
ttggcaatat ataaactttg gcttcatcag ttccattccg ggttcttctt tcttttcggg     180
gtttcgtccg tttttgtcgt gtgcgtgtgt gcatttcatc catgtcatgt tgtcatgtgc     240
attgcattgc atttgtgttg tcatgtgcat ccggtcccac tagtctcttc ctgttgtccg     300
tttcgagttc cgacgctctc tcacgtgccc gtggcatccc cgagtcggac ccgttatagt     360 ttaggggggag cagatgcaag cttttcttt ccatagccgg ccaaatgact accggatcat     420
cggtctactc tacctcaatt caccatttcg aactttatac agaaggtttt tccgtaccag     480
ctccttctac ctataccgca gttgaagcac ctaaaggtga atttggtgcc tttcttgtca     540
gtaatgggag taatcgtccc agggcctatc cgaaagagaa tccagtaccc cttggtcctg     600
aatatcagaa tagggcgaac gaacggcctc cgcggatatt tttgcttcgg aacaaaccct     660
gcaatcaaat agattgtccc aagggcgcca tattctagta gcccaagtta tgctattgaa     720
aattcgttcc tctatgcatg ctcatatgtt ttagattccc catcatgtgt actttgctgt     780
ggtacaaacc acttgccatg ttatgctttg aggtgactta aacttgctca caaacatgcc     840
atgataatac tgctgtttta acacttagtg aaatttcact aagtttggaa tctgtaatat     900
ccggatgcta tgtttgcttg ttgttctagg caaatccatg atagttttgg ggtgactatt     960
gatgtttcct tgttgtatat gttgttgtat atccattcat gccctctcat gctcatttcg    1020
gtggctgtag catatttaat tcttgctccc aagttgctat aaaatactgc tgtcaggttt    1080
ttgttgtcat gttcaaaatg ttgtagcttg ttgctattga tccatgcctc ctatggagat    1140
gctccaatgg aattgtttac tgtaggatat gtctatttca tgtccatgct tcttgtcatg    1200
atgtttgagt gatgtagagt atatacttct tgctccgaag ttgctatgtg gtgttatttt    1260
tagctttgct tgtttcttgt ttcgggtgta tcttttagcc cgttgctccg ttttgagcaa    1320
gtcctatatg aaacttgtgt gggttttgaa tgtaaattca taatatcatc ttgttaacat    1380
gttttgaagt atcttgcttg ttgcatattg tcatgttcct tgtgatgtat ctctgtgttt    1440
cctatgttgt cttgctgtgc atccttagtg catctgcagt gcttccttag tgcatcagcc    1500
atgcatcctg tagtttgcgc attgcatctt gtttgatttc gtgcctcgtg tgttttgtgt    1560
tgagtagagc cgaaagccga gaccgagtac gagaacgagg ttactaccga ggttgagaac    1620
gaggagccct cttacgatcc catcgacgac tcgacaggca agatgacctg acccagatat    1680
cattactatc tttgcctatt gctagaagtc tcgctcttta gcttattgcc acgatgccca    1740
```

```
tgtttgtctg tccgcctcct attgtaacca tgaatctgtc taaccaccct acctatgcaa      1800
acctttgttt ggctaagtat ttttttctg cccctctta tagcattgct agttgcagga       1860
gaagatttga agattcttgc ttcatgttga agcttgttgg gatatcacac tatatacact      1920
ctttaatgaa tcatctatat attggtaatg ggtggaagct gagcctcttg ctcgttgatt      1980
ttttccactc atgccccct aggaaccta ttaaaccggt tttatgttc ctgatttgt          2040 gttcctcaca tggttggggt tatgggaccc ccctcgataa aaccttagcg ctaaggcttt      2100
tccagcaagt cccaacattg gtactatttg cctaaacaac taaaacttgc cgagggagta     2160
attacccctt ggattttta atcaacccc ctgggccagt gctcgatttg agtgttggtc       2220
caaactagag ccacttgcgg tgccacccag ttcgcttggg tcttcggtat ctgtacgtac     2280
tgctcatcca gtcatggcct gagactagat acgcgcggct actgtcaggg tgtcgcacgc    2340
cgggaggatt tgctggatta gtcttacctt agcacagaat cttttggcac gggattccga     2400
ggatactcgg gccttccac cttgagttg cgacttcgcg gatcgtgggc ttgtcatgtg       2460
ccaagttgga accaccctgc agggttgttt ttgtttctaa agccgtgccc gcggttatgt     2520
ggcagatggg aatttgttaa tatccggttg ttgaaaactt gacaccatgt tcagacacac    2580
taccagcgtg agtaccgtga cggtcatttt ccgaaagggt tcgggaagtg aacatggggg    2640
ggttatgttt gtcgtgtttt agtttaggag attcgtgatc actttatcgt ctgaggcact    2700
tctcttctct ctctctttta cgtaagttag tgctagtgct gctgcaacct cttatttttt    2760
ttcttcagcc ttgttccaca cccaaggctt ggatagttgt gttacccggg aacgggattg    2820
ctgagtcctc tgtggctcac agattctaca ccacaccaga tgcaggtact caggtgatct    2880
attcaggtga cggcaccgag ctatactggg agtacgatga ggaacgtagc cgttactatg    2940
tgcactatcc cgacgatcag tagaggttc tactaggggc gattcagacc tgtggcttta    3000
tgtatgtttg gtatcttcat ttggatcttc acccgtagac ggttgtgatg ttaattgaat    3060 gatgttttc tatgtaatga attgtgtgac gtggcgagtg taagccaact atctttttg      3120 ccccccccc catttacatg agatgtgcaa agataccgaa cttgcgatca ttccagaatg    3180
ggcttatacc tttaagtcgt gcctcgacac gtaggaggta tagtcccatc ctgggcatta    3240
caagttggta ttcagagcct ctccgacct agaagccccc cactgattga tcgaatcgtt    3300
gacggttgag tctaggcaca cacttaaaat gttttgagtc ctatatatat atcggagagt    3360
aggatttctt ttgctcctca tctctttca tggtgaggac tcctgacgac tac              3413
```

<210> SEQ ID NO 5
<211> LENGTH: 2858
<212> TYPE: DNA
<213> ORGANISM: Secale cereale

<400> SEQUENCE: 5

```
gtagtcgtca ggagtcctca ccacgataaa gggatgagga gtaaaaagaa atcctactct       60
ccgatatata taggactcaa aacattttca tgtgtgtgcc tagactcaac cgtcaacgat      120
tcgatcagtc agggggctc tgtaatgccc cagatgtaac actttccaaa tatggcaata     180
tataaacttt gacttcatca attccattct gggctcttct ttcattttgg ggtttcttag     240
ttttgtcgtg tgcgtgtgtg catttcatcc atatcatgtt gtcgtgtgca ttgcattgcg     300
tttgtgttat aaattataac tgtcaggttt ttaacaacat gttcaatttg gcgtacttgt     360
tgctattgat ccatcctcc tatggagttg tttgctgtag gatatgtcta cttcacgtcc     420
atgcttattg tcatcatgtt tggttgctct agagtatata tttcttgctc caaagttgct    480
```

```
atgtggctgt taatttcagc tttgcattgt ttcttgtttc gtgtgtatgt gttgaaccgt    540
tgctccgttt tgagcgtgac ctatatgaaa cttgtgtgat tttcatgtag aatcatatat    600
catgttgtta acatgtttgg agtgtgtttt cttgatgttt gggtgcatct tgcacgttgc    660
catgttgact tgttttgctc ataccttcta gatcgtagct ctgaattaaa caaactttat    720
atgaaacttg actagaattt tgtgtagatc atcatggtgc atgttaactt gctgtttaac    780
aactttaact taaggttgtt cagatctgga ccaacttcaa catatgcata tgaggactac    840
ggattgctat atgtgtattc cggcctcatt taaacttgtt gtcttgtgtt gttcttgtgt    900
gcttcatccc ttgacatgta ttgcatcata tatgcaccat acttgcacca tgttgattgc    960
acattgcacc ttgtttgata tcgtgccatg ttgtgttctt gtgttgagta gagccgagag   1020
acgagaccga gaacgaggtt actaccgagg ttgagtacga ggagccgtgt tacgatccca   1080
tcgatgactc aacaggcaag atgacctgac ctagatatca ttactatctt tgcctattgc   1140
tagatgtctc gctctttagc tcattgcatc gatgcccatg tttgtttgtc agcctcctat   1200
tgtaaccatg aatctgtcta atcacccaac ctagcaaacc tttgtttggc tacgtaagct   1260
tcgctcagcc cctcttatag cattgctagt tgcaggagaa gatttgaaga ttcttgcttc   1320
ttgttgaagt tattgttggg atatcacact atataaaact cttaaactaa atcatctata   1380
tattggtaat gggtgggagg ctaagctctt gcttggtggg tttccactca tgccgcccta   1440
ggaaccgttt aaaccggtgt tatgtccttg attatgggtc ctaacacggt tggggtttgg   1500
gaccccctcga taacctactt agcgctaaac cttttccagc aaggcccgac atgggttttc   1560
atttgcctaa tagctaaaac ttgcataggg ctttgcaaac ccgagttctt aatcaacaac   1620
ccgggccagt gctcctcatg agtgtttgtc caaactgggg ggttatgcgg ggccaccacg   1680
aggaaacccg aggattggtt ttacctgtag gatcgcccat ccggtcgtgg cctgagacta   1740
gatatgcgcg gctattgtca gggtgtcggc acgccgagag gtcttgctgg aattagtttt   1800
accttagtca gaatatcttg agcacgggat tccgagaata ctcgggtctt cccaacttgg   1860
agttgcgact cgcagatcgt gagcttgtaa tgggctaagt tgggacaccc ctgcaggttt   1920
tgaactttcg aaagccgtgc ccgcggttat gtggcagatg ggaatttgtt aatatccgat   1980
tgttgaaaac ttgacaccat gttcagaaca cactaccagc gtgagtaacc atgacggtca   2040
tttaccgaca agggttcagg aagtgaacac ggtggggtta tgattgacgt gcttagatat   2100
gatcacttca tgatcacttt gacgttcgtg gcacttctct tctcgctcta aacacgtaag   2160
gtagtgctag tgcagctgca acccttgtcc ttcttcagcc ttgttccaca cccaaggctt   2220
agatagtttt gttacgcggg gaacggaatt gctgagtctc cgtggctcac aatttctaca   2280
caacactaga tgcaggtact atggtggact acacaggtga cggcaccgag ctgtactagg   2340
agttcgatga agaacgtaat cgatactatg tgcactatcc cgatgatcag tagtggtttc   2400
taactagggg cgattcggac cttgtggctt tatttatttg gtatgtttca tttgggatct   2460
tcgtccggta gtcggactgt tgatgttatt tgggatgatg atttgcttat gtaatgtaat   2520
tgtgtacgcg tggcgagtgt aaagccaact attcgttcta caaatttcat acctatttt   2580
tacatggagt cgtgcaaaca taccatactt ggaggatcat tctagtatgg gcttacccttt   2640
tccagtcggt cctcgaacgg taggaggtaa ccccatattg ggcatacaag tgggtttcag   2700
agccttctcc gacctagaag ccccccactga ttgatcgagt cgttgacggt tgagtctagg   2760
cacacacttg aaaatgtttt gagtcctata tatatatcgg agagtaggat ttcttttgct   2820
```

-continued

```
cctcatctct tttcatggtg aggactcctg acgactac                          2858
```

<210> SEQ ID NO 6
<211> LENGTH: 3697
<212> TYPE: DNA
<213> ORGANISM: Secale cereale
<400> SEQUENCE: 6

```
gtagtcgtca ggagtcctca ccatgaaaaa ggatgagaag caaacagaaa tcctactctc     60
cgatataaat atagaactca aaacattttc aagtgtgtgc ctagactcaa ccgtcaacga    120
ttcgatcagt cagtgggggc ttctaggtcg agaaggctc tgaataccaa cttgtaatgc     180
ccaggatgga tttatgcctt taagtcgtgc ctcgacacgt aggaggtata actccatcct    240
ggggcattac agctgtggag agtggcgtga ggaaaactaa catccttcct cttctgaata    300
ctcattctgc caagctcagt atttggggca tcatgaaatt cagtccgaca gtttaaatgg    360
aagaagtccc gaaatagctc cactgttggc tcctcttgca gataggcttc acagaagact    420
ttggagttgc agatatttga tacagagttg aacctatgt cttggggatg agctgaaaa      480
tttgctaaca tgtcacagaa aaactttgac ccttggaggg ttaaattccc gggacaagtg    540
atcaaataaa gacgacaatt ctccctcct tgggctttgg aggacactct tttccgggag     600
ccctccagtg aaggacatcc tttgggccta agcgccaat tgaggcatct tttccaaatc     660
ggcctcagtg atccgggatg ggacccagtt gctggagaca aactgtttgg ctgcggtagt    720
catcttttca aaagggaaag ctgaaaatac aataaagatc cggtttatga tctacgcaga    780
cttaaaaccg gtatgctcta tgaaggtact gatctaaatg gcggtttatg caggggccta    840
atggtatata tcgaatgaaa tatccggaac atctataacc atgacatcta ccggattatg    900
aagtgtgaaa ggaaaagtta aaccgccaac acaggcagat aaggcgcaga tctaaagttt    960
ggggaaacaa ctttcatgca agcagcaatg agatacagat ctgcaacata tggaaaatac   1020
agaaataatt ccaagtgata ttcagcagac gcgatgaaag tcctaaacag atttagtttt   1080
tctagcagta tggggagagg taagattaca atgacggagc ggattcttgc ttacggtggt   1140
tgacctaaag ggggggagct atggctaaat actatctatg gcaaagaacc gcgagaacag   1200
ggactcatct acgagctcgc atgaaaccct agaacagaga tctataagaa ggggagaaca   1260
agatgtaccc gagacgacgg gtgcggagag gcgctggcaa gtttctggaa gcgttcaggt   1320
tgatgcagcg accgggctcg acgaagacgc ataactcgac ggatggcggc ggactcgagc   1380
gctgaagaac agaggaagaa gagaaagga ggaaaagaga tgaccctcgg ccctatttat    1440
aagccaaagg gataaaacga caggcgcggg aatcgaggaa ccaaagggat aaagcggata   1500
tggacgatac tattacctcg atcttcgcag ttttaatgaa taaaggtaaa aaacaggtac   1560
aagcattaaa tgcgcagatg gcgtcatggt ggtttaaagt gatctgagga gatgacgtca   1620
cgccggttta caaagcatgc tggagctgcg gagaggaaga tatgtaaaga ctttgataga   1680
ttgacatgaa aaggttcaaa tcaatctggg gcgtaatgt cagggatgtt tctaccacag    1740
tataaacgcc aggtgggcgg gtttatgtta caagattacc ttatcaaagg cccagcgggt   1800
atgaggtaga agatttcagc ccaagaggtt tagagcccaa gtgttagggc ccatgatttg   1860
taaaccgcca tgctatgtaa tgtgagatgt aagatagaaa gagtagagac cagggcgaca   1920
tgattatgag ccggcctccg gactctttaa accggactgg gcgtcacctc ttatataaag   1980
ggacgacccg ccgattgttc aaggacagac aactacaact cgagatacag gccaagatgt   2040
gatcgctccc tggtcatcaa aaccctagca atacacacca aactagacgt aggctttac    2100
```

-continued

```
ccttcatcga aggggccgaa ctagtataac cccctatgtc cttgtctgct ttaaccccctt      2160 taagctaacc cgtagcgatg gcctcacgac taagtccttt tgctaggaca tctgccgtga      2220
caaaaccacg acaggaaggc ttggcctttt tcttggtgtt ttgttccact catgccgcct      2280
taggatccga taaactggtg ttatgttcct tgatattgcg ttcctaacac ggtttggggtt     2340 tatgggcccc cctcgataat tcgctctgtt taaagctttt ccagcaaggc ccaaccttgg      2400
ttttaccatt tgcctaataa ctaataattg catagggagt aattaacccg tggattctta     2460
atcaaccctc aggccagtgc tcctcatgag tgttggtcca aactagagcc acttgcgttg      2520
ccacctgggg caactcgggt ttttggctgt catacgtagt gttcatccga tcgtcgcctg     2580
agacgagata cgcgcagctg tttttcaggtg tcgaaatgtc gggagtcttg ctggattagt    2640
tttactattg tcgaaatatc ttgagcacgg gatttcgaga aagactcggg tcttcccaat    2700
ttggagttgt acccccccctg atcgtgagag cttgtgatgg gctaagttgg acatccttgc   2760
aaggttatga tctttcgaaa gccgtgccca cggttatgtg gcagactgga gttgttaata     2820
tccggttgta gataacttga caccataact caataagaat acactaccta tgtgattaac     2880
cgtgatggtc tctttttgaa ggggttcgga aagtgaacac gatgggttat gtatgaacat     2940
aagtagatag gatcacttct tgatcactac tagttgcgaa cgttggcata tatttctcgc     3000
tctgacttca taagctagca ccataaaatg attagtgctt gttgcagcca ctttacatcc     3060
tctccacacc taaaagcctt gatagttttg atacccggga acaaggttgt tgtgtccccg     3120
tggctcacag tttactacac aaacatgtgc aggtacatca gagtttgact caggagacgt    3180
gcaagagctc tagcgggagt ttgatgaaga gtgtgggtgt atgtacgtga cgtaccccga     3240
cgatcagtag tggttcctac tagggccgat cgggattagc ttgtgtataa aatttttctt     3300
cgtttgattt cgttcgtagt cggactctgt gttctttgga tgaatgtatg tttattgtat    3360
taattgtgtg acgtggcgag tgtaagccaa ctattaaact ctctttcatc atgttcatta    3420
catgggttgt gtaaagatac catgtttgag accattccag aatgcggtta tgactctaag    3480
gtgtgcctcg gcacgtagga cctatagccg catcttgggc attaaaagtt ggtaatcaga    3540
gccttccccg acctaggagc ccctgcttga acgaaccact ggcgatgttg agtttagaaa    3600
caaatattgt tttgagtctt aggaaatatgt atatcggaga gtacgaattc ttttactcct   3660
tatccccttc gtcgtggtga ggactcctga cgactac                              3697
```

<210> SEQ ID NO 7
<211> LENGTH: 694
<212> TYPE: DNA
<213> ORGANISM: Secale cereale

<400> SEQUENCE: 7

```
ggcacgaggg tacgagtccg agacgaccaa gtacgactac gaccgggacc gagaccggca       60
agtacatcta cggccgagta caccacgaca cgatgacgtg aacaactaca tgacccgaca      120
agtaccacta catgtacaag tacctcgacg accgaacggc tacgagctcg agaacgacta      180
ctcggagacc caagtaccac taccgtcgcc cgaacgtcta cttccctcta cggccgtgta      240
caactacttc cctctactac ggctacgtcc ctctacgatc ccgaaccgcc ccgaaacgca      300
cgcttcaaag cttcggtttc gttcgggagt tgtgaggatc cgctcgactg tgttgctccg      360
tcttcttctt ggatccgttc ttcttccttt gtggaatccc agatgcaggt tcagccgagc     420
tcgatgcagg agctggttca gtgcttcccc aggagcttgt tgaagatcgt ggctgtttgc    480
```

-continued

| | |
|---|---|
| ttgagacgtt tcgatgttca gtagtggttt ctactaggat tcgatcctga cctgtggctt | 540 |
| ttgttgtttt ggtatctttc tttttggttct tcacccgtag tcgggttgtg atgttttgaa | 600 |
| tgatgattgc ttatgtaatg tattgtgtga agtggcgagt gtaagccaac tatcctcttt | 660 |
| tgcattttaa tccctctttt acatgagttg tgcg | 694 |

<210> SEQ ID NO 8
<211> LENGTH: 726
<212> TYPE: DNA
<213> ORGANISM: Secale cereale

<400> SEQUENCE: 8

| | |
|---|---|
| ggcacgaggg tacgagtccg aggatccgtg aacatctaca aaacgcccga gttcgtctac | 60 |
| cgacgcccgg gaaaacgaca agtacccta catccgtgta cgacacgtgt acctcgacga | 120 |
| ccgaacggct acgagctcga aacgactac tcggagaccc aagtaccact accgtcgtcc | 180 |
| ggaagcacca tgtaccacaa ccgtcgccga aacctcaagt acctctacga acgaacggaa | 240 |
| cgagtacctc taccgtcgcc cgagaacaac tacttccctc tacggccgtg aacgactact | 300 |
| tccactacga actcgaaccg ccccgaaacg agtgtttcga agcttcggtt tcgttccgga | 360 |
| gttgtgagga tccgctcgac tgtgttgctc cgtcttcttc ttggatccgt tcttctccct | 420 |
| tgtggaatcc cagttgcagg ttcagccgag tttgatgcag aagttggttc agttcttcat | 480 |
| caggagctcg atgaagagtg tgtccgtttg cttgtgacgt ttcgatgttc agtagtggtt | 540 |
| tctactagga ttcgatcctg acctgtggct ttatgttgtt ttggtatctt ttcttttggat | 600 |
| cttcacccgt agtcgggttg tgatgttttg aatgatgatt gcttatgtaa tgtattgtgt | 660 |
| gaagtggcga gtgtaagcca actatctcct tttgcaattt aatccctctt ttacatgagt | 720 |
| tgtgcc | 726 |

<210> SEQ ID NO 9
<211> LENGTH: 728
<212> TYPE: DNA
<213> ORGANISM: Secale cereale

<400> SEQUENCE: 9

| | |
|---|---|
| ggcacgaggg tacgagtccg agacgaccaa gtacgactac gaccgggacc gagaccggca | 60 |
| agtacatcta cggccgagta caccacgaca cgatgacgtg aacaactaca tgacccgaca | 120 |
| agtaccacta catgtacaag tacctcgacg accgaacggc tacgagctcg aggacgacta | 180 |
| ctcggagacc caagtaccac taccgtcgcc cgaacgtcta ccgtcgcccg aacgactacc | 240 |
| gtcgcccgaa cgtctacttc cctctacggc cgtgtacaac tacttccctc tactacggct | 300 |
| acttcctcta cgtctcgaac cgccccgaaa cgcacgcttc aaagcttcgg ttccgttccg | 360 |
| gagttgtgag gatccgcttg actgtgttgc tccgtctact tcttggatcc gttcttctcc | 420 |
| cttgtggatt cccagatgca ggctcagccg agtttgatgc aggagttgga tcagttcttc | 480 |
| accaggagct cgatgaagag tttggctgtt tgctcgtgac gtttcgatgt tcagtagtgg | 540 |
| tttctactag gattcgatcc tgacctgtgg ctttatgttg ttttggtatc ttgcttttgg | 600 |
| atcttacccct tagttgggtt gtgatgttct gattgatgtt atgcttatgt aaagtattgt | 660 |
| gtgaagtggc gagtgtaagc caactatctc ttttgcatt ttaatccctc ttttacatga | 720 |
| gttgtgcc | 728 |

<210> SEQ ID NO 10
<211> LENGTH: 665

<212> TYPE: DNA
<213> ORGANISM: Secale cereale

<400> SEQUENCE: 10

```
ggcacgaggg tacgagtccg agacgaccaa gtacccctac gccaagtacc cctacgcttg    60
acgacccgag tacctcgaca cgaacggcta cggaacaagt accacgacac gtgaacggct   120
accgtcgccc ggaaacgaag gtttcgccaa gtaccactac acgacgccac gagtacctct   180
accgtcgccc gagtacaact acttcctcta cttcccacga cgacccgtg aacggctcct    240
tccactacgt ctcgaaccgc tccgttaacg cacgcttcga agcttcggtt tcgttccgga   300
gttgtgaggt ttccgctcgt ttgttgctcc gtcttcttcg tggatccgtt cttctcctct   360
gtggaattcc agttgcaggt ccagccgagt tagatgccgg agctggttca gtgcttcacc   420
aggagctcga tgaagagtgt ggccgtctgc ttgagacgtt tcgatgttca gtagtggttt   480
tctactagga ttcgttcctg gcctgtggct ttatgttgtt ttggtatctt tctttggttc   540
ttcacccgta gccgggttgt gatgttctga atgatgattg cttatgtaat gtattgtgtg   600
aagtggcgag tgtaagccaa ctatcctctt tgcttttta  atccctcttt tacatgagtt   660
gtgcc                                                               665
```

<210> SEQ ID NO 11
<211> LENGTH: 395
<212> TYPE: DNA
<213> ORGANISM: Secale cereale

<400> SEQUENCE: 11

```
ggcacgaggt ttcgagtccg agttcgagca cgatcacgag gtttccaacg aggttgagca    60
cgaggaccct tcttacgatc cgaacgactt cacttcagat gcaggtccag ctgtgagcta   120
tccaggtgat ggcaccgagc tggattggga gtacgacgag gagcgtagtc ggtactatgt   180
gggatatccg gatgatcagt agtgaagact tctactagga ttcgatccgc ctgtggttta   240
tttatctaag tttggtatct tgcatttggt tttgccctta gagggttgtg atattcttat   300
gtatgatgat tgagacatgt tatgtaattg tgtgacgtgg cgagtgtaag ccaactattt   360
atgtttacaa tcccctcttt tacatgagtt gtgcc                              395
```

<210> SEQ ID NO 12
<211> LENGTH: 1597
<212> TYPE: DNA
<213> ORGANISM: Secale cereale

<400> SEQUENCE: 12

```
ggcacgaggg tacgagtccg agcacgaggt ttccaacgag gttgagcacg aggacccttc    60
ttacgatccg aacgacttct cttcaggcaa gatgaccgaa ccccgataac attactatct   120
ttgcctattg ctagtagttc cgctctatag tattgcctcg atgcccatgt tcttcctgtc   180
agcctcctat ttgtaaccgt tgccatgttt aaccacccct cctacgcaaa ccgttgcttg   240
gctaagtacg cttcgctcag cccttcttat agcattgtta gttgcaggtg aagattgaag   300
acgcttgctt catgttgaag tttggttggg ttatatcaca ctatataaat gttttaatga   360
aatcatctat atattggcaa gggtggaagg ctaagccttt tgcttggtga tttgttccac   420
tcatgccgtt aggaaccgta taaccggtg ttatgttcct tgattatgcg ttcctaacac    480
agttggggtg tatgggaccc cctcgataaa ccgctaagtg ctaagtcttt tccagcaagt   540
cccaacattg gtactatttg cctaaacaac ttaaacttac cgagggagta attaacccga   600
```

```
ggatttaatt aattcaaccc ccctgggcca gtgctcgact tgagtgttgg tccaaactag      660
agccacttgc ggatgccacc cagttcgctg ggatcttcgg catctgtacg tactgctcat      720
ccggtcgtgg cctgagacta gatacgcgcg gctactatca gggtgtcggc acgccgggag      780
gatttgctgg attagcctta ccttagttcg gtttaacttg agcacgggat tccgagaata      840
ctcgggtctt ctcactttgg agttgcgact ccgcagatcg tgagcttgtc atgggctaag      900
ttgggacacc cctgcagggt taagaacttt cgaaagccgt gcccgcggtt atgtggcaga      960
tgggagcttg ttaatgtccg gttgtagata acttgacaca atgtttcaat acactaccag     1020
cgtgagtacc gtgactgtca gtttccgaat agggattcgg gagttgaaca cggtgggggtt    1080 atgtctgttg agttctagct aggatcactt agtgatcatc tcttgaccgt ggcactcctt     1140
ttctcgctct ctttaacgca agctagttgc tagttgctgc tgcagacact tgttcttttc     1200
ttcagccttt cctcacccca aaggcttaaa tagtcttgtt acccgggaac gggattgctg     1260
agtcctctgt ggctcacagt tacttcacca caccagatgc aggtccagtt atgagctatc     1320
caggtgatgg caccgagcta gactgggagt acgacgagga gcgtagccgt tactatgtcc     1380
gttatcctga tgatcagtag tggagactct tactaggatt cgatcctcct gtggtttatt     1440
tatttcagtt tggtattttg ctatttggat tttaccctta gagggctatg atactcttat     1500
gtatgatgtt tgaggcttgt actgtagatt ctgtgacgtg gcgagtgtaa gccaactatt     1560
tttctgttta ctatcccctc tttacatga gttgtgc                               1597
```

<210> SEQ ID NO 13
<211> LENGTH: 117
<212> TYPE: PRT
<213> ORGANISM: Secale cereale

<400> SEQUENCE: 13

```
Met Thr Arg Gln Val Pro Leu His Val Gln Val Pro Arg Arg Pro Asn
 1               5                  10                  15

Gly Tyr Glu Leu Glu Asn Asp Tyr Ser Glu Thr Gln Val Pro Leu Pro
             20                  25                  30

Ser Pro Glu Arg Leu Leu Pro Ser Thr Ala Val Tyr Asn Tyr Phe Pro
         35                  40                  45

Leu Leu Arg Leu Arg Pro Ser Thr Ile Pro Asn Arg Pro Glu Thr His
     50                  55                  60

Ala Ser Lys Leu Arg Phe Arg Ser Gly Val Val Arg Ile Arg Ser Thr
 65                  70                  75                  80

Val Leu Leu Arg Leu Leu Leu Gly Ser Val Leu Leu Pro Leu Trp Asn
                 85                  90                  95

Pro Arg Cys Arg Phe Ser Arg Ala Arg Cys Arg Ser Trp Phe Ser Ala
            100                 105                 110

Ser Pro Gly Ala Cys
        115
```

<210> SEQ ID NO 14
<211> LENGTH: 19
<212> TYPE: DNA
<213> ORGANISM: Secale cereale

<400> SEQUENCE: 14

```
tgtgacgccc gagaccgac                                                    19
```

<210> SEQ ID NO 15
<211> LENGTH: 10

```
<212> TYPE: DNA
<213> ORGANISM: Secale cereale

<400> SEQUENCE: 15
tccagaagat                                                             10

<210> SEQ ID NO 16
<211> LENGTH: 20
<212> TYPE: DNA
<213> ORGANISM: Secale cereale

<400> SEQUENCE: 16
gtcccatcct gggcattaca                                                  20

<210> SEQ ID NO 17
<211> LENGTH: 12
<212> TYPE: DNA
<213> ORGANISM: Secale cereale

<400> SEQUENCE: 17
atcattctag ga                                                          12

<210> SEQ ID NO 18
<211> LENGTH: 28
<212> TYPE: DNA
<213> ORGANISM: Secale cereale

<400> SEQUENCE: 18
tgttctacta ccgtcgcccg gaaaagac                                         28

<210> SEQ ID NO 19
<211> LENGTH: 10
<212> TYPE: DNA
<213> ORGANISM: Secale cereale

<400> SEQUENCE: 19
taccgtcgcc                                                             10

<210> SEQ ID NO 20
<211> LENGTH: 20
<212> TYPE: DNA
<213> ORGANISM: Secale cereale

<400> SEQUENCE: 20
gtcccatcct gggcattaca                                                  20

<210> SEQ ID NO 21
<211> LENGTH: 12
<212> TYPE: DNA
<213> ORGANISM: Secale cereale

<400> SEQUENCE: 21
atcattctgg ga                                                          12

<210> SEQ ID NO 22
<211> LENGTH: 38
<212> TYPE: DNA
<213> ORGANISM: Artificial Sequence
<220> FEATURE:
<223> OTHER INFORMATION: Primer for PCR (726RT38)

<400> SEQUENCE: 22
tttttttttt ttttggcac aactcatgta aaagaggg                               38
```

```
<210> SEQ ID NO 23
<211> LENGTH: 22
<212> TYPE: DNA
<213> ORGANISM: Artificial Sequence
<220> FEATURE:
<223> OTHER INFORMATION: Primer for PCR (726-5F)

<400> SEQUENCE: 23
ggcacgaggg tacgagtccg ag                                          22

<210> SEQ ID NO 24
<211> LENGTH: 23
<212> TYPE: DNA
<213> ORGANISM: Artificial Sequence
<220> FEATURE:
<223> OTHER INFORMATION: Primer for PCR derived from adjacent region of
      Revolve-2

<400> SEQUENCE: 24
gtagtcgtca ggagtcctca cca                                         23

<210> SEQ ID NO 25
<211> LENGTH: 26
<212> TYPE: DNA
<213> ORGANISM: Artificial Sequence
<220> FEATURE:
<223> OTHER INFORMATION: Primer for PCR derived from internal region of
      Revolver-6

<400> SEQUENCE: 25
atagctccac tgttggctcc tcttgc                                      26

<210> SEQ ID NO 26
<211> LENGTH: 26
<212> TYPE: DNA
<213> ORGANISM: Artificial Sequence
<220> FEATURE:
<223> OTHER INFORMATION: Primer for PCR derived from internal region of
      Revolver-6

<400> SEQUENCE: 26
cattcatcca aagaacacag agtccg                                      26

<210> SEQ ID NO 27
<211> LENGTH: 25
<212> TYPE: DNA
<213> ORGANISM: Artificial Sequence
<220> FEATURE:
<223> OTHER INFORMATION: Primer for PCR

<400> SEQUENCE: 27
gcctttcggc cttcctctca ggcgg                                       25

<210> SEQ ID NO 28
<211> LENGTH: 25
<212> TYPE: DNA
<213> ORGANISM: Artificial Sequence
<220> FEATURE:
<223> OTHER INFORMATION: Primer for PCR

<400> SEQUENCE: 28
gtacttggca tcggtagatg ttcgg                                       25
```

REVOLVER-2: A NOVEL TRANSPOSON-LIKE ELEMENT FROM RYE

BACKGROUND OF THE INVENTION

1. Field of the Invention

The present invention relates to Revolver which is a novel transposon-like element and its structural mutants, as well as a method of utilizing the same.

2. Description of Related Art

Ryes (*Secale cereale*, 2n=2x=14) and its related species have genes responsible for disease resistance and environmental stress resistance, and they are important genetic resources for productive breeding of wheat and triticale. For example, the genome size of rye reaches to 7.8 Gb, and the size of short arm of the chromosome is comparative to 2 folds of that of *Drosophila* genome. Furthermore, the genes which is involved in protein synthesis occupies only several percents of the genome, and repetitive sequences that repeat same nucleotide sequences occupy more than 90% of the genome.

A transposon or a retrotransposon is one kind of transposable element existing in chromosomes or plasmids of prokaryotic or eukaryotic organisms. In the nucleotide sequences of the transposon or the retrotransposon, several hundreds to a thousand and several hundreds of nucleotides are inversely repeated at both terminals, and the inverted repeat sequences and a region sandwiched by the sequences compose one unit. Such a transposon has been a driving force of genome construction and evolution beyond species of organism.

In rice and maize, transposon-like elements which are transposable genetic element have been utilized as tools for genetic analysis and development of DNA markers. In the breeding of wheat and triticale, when one intends to transfer genomes and genetic information across species, if a transposon specifically present in the genome of a useful resource plant could be obtained, it would be effective as a tool for development of DNA marker. However, the structures of transposons found so far are widely common among living creatures. Moreover, transposon has not been discovered in wheat and the like, and there has been no tool useful in development of DNA markers for wheat and the like.

SUMMARY OF THE INVENTION

Thus, the present inventors have attempted to clone a transposon-like element specifically present in the rye genome but not present in the wheat genome, for the purpose of breeding wheat exhibiting resistance to disease and environmental stress. If a transposon obtained has been amplified and dispersed in the rye genome after differentiation into wheat and rye, it can be utilized for detection and identification of the rye genome introduced into the wheat genome, construction of DNA library, gene amplification, probes for DNA polymorphism and entry points of PCR, identification of exogenous genes by chromosomal in situ hybridization, and the like. Therefore, the object of this invention is to obtain a novel transposon-like element specifically present in the genome of the rye and the like.

According to the present invention, DNA sequence of Revolver, a transposon-like element comprising nucleotide numbers 381 to 3422 shown in SEQ ID NO:1 in the sequence listing, and DNA sequences of the cDNA and structural mutants thereof have been provided.

The nucleotide sequence of the transposon-like element Revolver is conserved among rye genus and related species thereof but it is not present in common wheat. Revolver has been amplified in some related species in the process of evolution from ancestral species of the wheat and disappears in common wheat. Therefore it is useful as a genetic marker for the genome of wheat related species. More specifically, the transposon-like element of the present invention is useful as a tool for development of probes or primers, as well as chromosomal markers, which can contribute to molecular breeding of useful resource plants.

These and other advantages of this invention will be apparent from a reading of the following detailed description and the drawings.

DETAILED DESCRIPTION OF THE INVENTION

Figure 1:
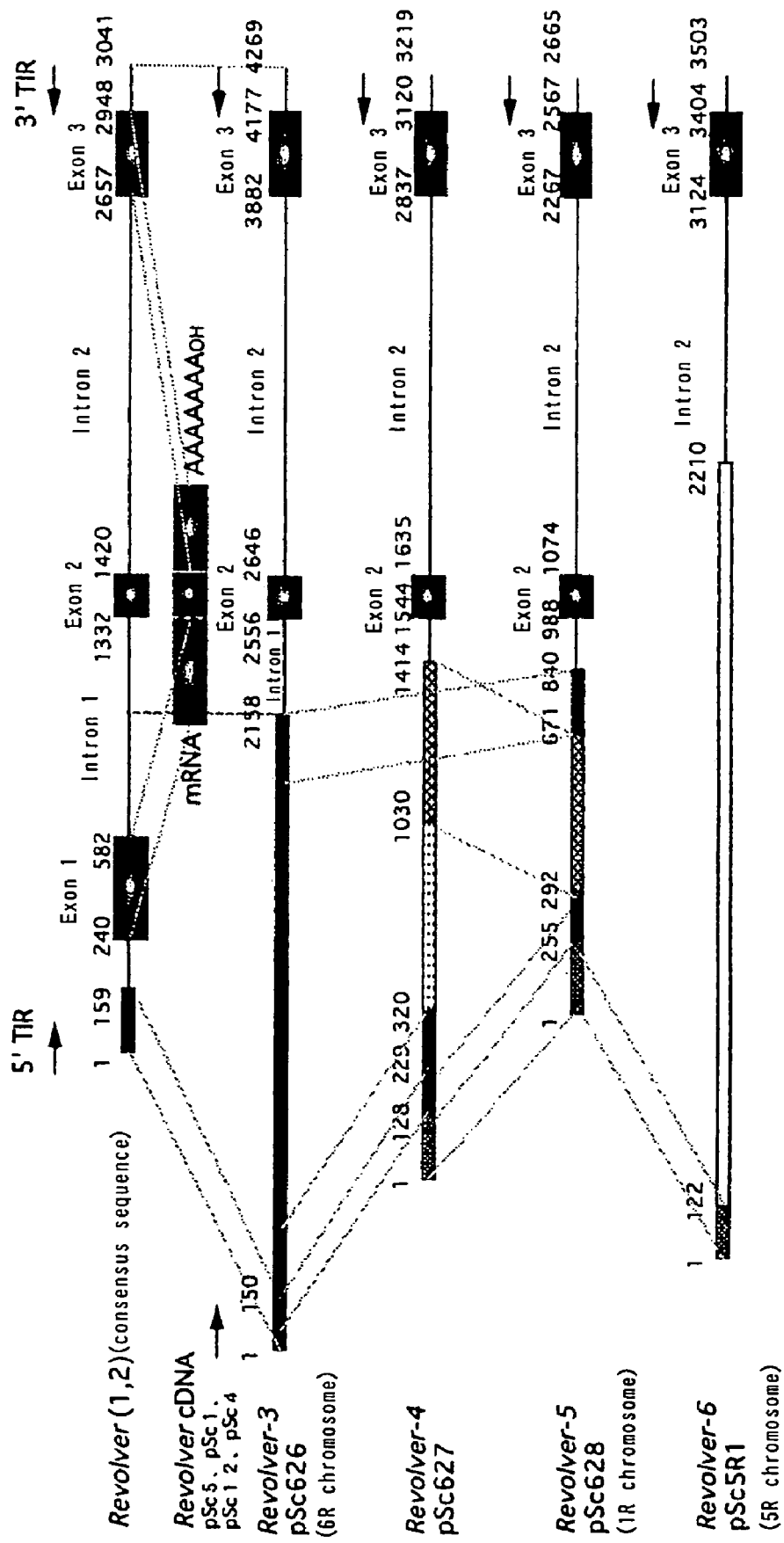
FIG. 1 is a schematic view showing structures of Revolver and non-autonomous elements thereof.

As shown in the following examples, the present inventors have cloned a repetitive sequence specific for the rye genome and obtained a novel transposon-like element, by isolating DNA specific for the genome using subtraction method of homologous sequences. Thus, the present invention relates to the transposon-like element Revolver comprising 3041 nucleotide pairs. Revolver according to this invention is an element having a novel nucleotide sequence, but the portions of nucleotide sequence similar to the transposon have been found, therefore, herein Revolver is refereed to "transposon-like element". The transposon-like element according to this invention comprises the nucleotide sequence represented by nucleotide numbers 382 to 3422 shown in SEQ ID NO:1 in the sequence listing.

The nucleotide sequence shown by nucleotide numbers 1 to 4000 in SEQ ID NO:1 in the sequence listing corresponds to the sequence where 5'-flanking region and 3'-flanking region are added to the sequence of the above-mentioned transposon-like element Revolver. In SEQ ID NO:1 in the sequence listing, the region of nucleotide numbers 1 to 381 represents the 5'-flanking region and the region of nucleotide numbers 3423 to 4000 represents the 3'-flanking region.

The transposon-like element Revolver contains three exon regions and two intron regions. In SEQ ID NO:1 in the sequence listing, the region of nucleotide numbers 382 to 539 represents 5'-consensus region including a inverted repeat sequence (TGTGACGCCCGAGACCGAC: SEQ ID NO:14) and a subterminal repetitive sequence (TCCAGAAGAT: SEQ ID NO:15) which are characteristic for transposon terminals. The region of nucleotide numbers 621 to 962 represents the first exon region, the region of nucleotide numbers 963 to 1712 represents the first intron region, the region of nucleotide numbers 1713 to 1800 represents the second exon region, the region of nucleotide numbers 1801 to 3037 represents the second intron region, the region of nucleotide numbers 3038 to 3328 represents the third exon region, and the region of nucleotide numbers 3329 to 3422 represents 3'-consensus region including a inverted repeat sequence (GTCCCATCCTGGGCATTACA: SEQ ID NO:16) and a subterminal repetitive sequence (ATCAT-TCTAGGA: SEQ ID NO:17) which are characteristic for transposon terminals.

It is possible to study genomic evolution by performing Southern hybridization and PCR using the nucleotide sequence of this Revolver or its flanking region as a probe or a primer. Herein "transposon-like element containing regulatory element" means the sequence where the nucleotide sequences of the 5'-flanking region and the 3'-flanking region are added to the nucleotide sequence of the transposon-like element.

It is possible to obtain homologs corresponding to Revolver of the present invention from any kinds of organisms using the nucleotide sequence obtained from the transposon-like element of the present invention as a probe or a primer. Also, it is possible to apply it for the purposes such as chromosome mapping described below in detail. It is possible to obtain such a probe or primer from not only the transposon-like element but also from above-mentioned 5'-flanking region or 3'-flanking region. Thus, the nucleotide sequences of the transposon-like element containing regulatory element of the present invention provides the nucleotide sequences of the transposon-like element including the flanking regions which can provide the useful probe or primer. Not only the nucleotide sequence of the transposon-like element but also the nucleotide sequences of the flanking regions which provide useful probe or primer are also within the scope of the present invention.

Moreover, it is also possible to detect rye chromosome by performing fluorescence in situ hybridization (FISH) using this probe. In the following examples, FISH analysis was performed using a Revolver probe and dot signals were detected.

Moreover when PCR is performed using the internal sequences of Revolver as primers, DNA fragments of various sizes are amplified from the genome. These fragments can provide markers for chromosomes and genes, because these fragments are located on chromosomes and can be mapped by DNA polymorphism. Genetic markers has been developed by using the sequences of retrotransposons, utilizing elements scattering in the genome as primers. The primers obtained from the internal sequence of Revolver can provide novel tools for development of such chromosomal markers and genetic markers.

According to gene recombination technology, it is possible to induce an artificial mutation at a specified site of basic DNA without altering basic property of the DNA or to improve the property. It is possible to artificially modify the DNA having the native sequence provided by the present invention without altering the property of the transposon-like element of the invention, and such mutant DNA is also included within the range of the present invention.

In the present invention, the nucleotide sequence of such mutated DNA has 60% or more, preferably 70% or more, more preferably 80% or more, still preferably 90% and still preferably 95% or more homology to the nucleotide sequence represented by SEQ ID NO:1 in the sequence listing, and the mutatated DNA hybridizes with the nucleotide sequence represented by SEQ ID NO:1 in the sequence listing under stringent conditions. Such a mutatated DNA is also within the scope of the present invention so long as it has the property as the transposon-like element of the invention. Similarly, in the DNA represented by SEQ ID NOs: 2 to 12 in the sequence listing, mutant DNAs thereof are also within the scope of the invention.

The condition for hybridization can be selected by a skilled artisan ad libitum. For example, hybridization can be performed by the following procedure. DNA molecules or RNA molecules to be tested are transferred onto a membrane, then the membrane is hybridized with a labeled probe in a proper hybridization buffer. The hybridization buffer may comprise, for example, 5×SSC, 0.1 (weight)% N-lauroylsarcosine, 0.02 (weight)% SDS, 2 (weight)% of blocking reagent for nucleic acid hybridization, and 50% formamide. The blocking reagent for nucleic acid hybridization may comprise, for example, a buffer (pH7.5) containing 0.1M maleic acid and 0.15M sodium chloride and commercially available blocking reagent for hybridization dissolved into the buffer at the concentration of 10%. The 20×SSC solution may comprise 3M sodium chrolide and 0.3M citrate, and the SSC solution may be preferably utilized at the concentration of 3 to 6×SSC, more preferably at the concentration of 4 to 5×SSC.

The temperature for hybridization may preferably be 40 to 80° C., more preferably be 50 to 70° C., further more preferably be 55 to 65° C. Incubation may be performed from several hours to overnight, then washed by a washing buffer. The temperature for washing may preferably be room temperature, more preferably it may be the temperature used for hybridization. The formulation for the washing buffer may preferably comprise 6×SSC and 0.1% (weight %) SDS, more preferably may comprise 4×SSC and 0.1% (weight %) SDS, further preferably may comprise 2×SSC and 0.1% (weight %) SDS, more further preferably may comprise 1×SSC and 0.1% (weight %) SDS, most preferably may comprise 0.1×SSC and 0.1% (weight %) SDS. The membrane may be washed by such washing buffer, then DNA molecule or RNA molecule may be distinguished by the hybridization with the labeled probe.

Furthermore, the present inventors obtained a transposon-like element Revolver-2 comprising 2929 nucleotide pairs from a clone different from above-mentioned Revolver. The transposon-like element Revolver-2 of the present invention comprises the nucleotide sequence represented by nucleotide numbers 377 to 3305 shown in SEQ ID NO 2 in the sequence listing.

The nucleotide sequence represented by nucleotide numbers 1 to 3528 shown in SEQ ID NO:2 in the sequence listing is the sequence where 5'-flanking region and 3'-flanking region are added to the above-mentioned transposon-like element Revolver-2. In SEQ ID NO:2, the region of nucleotide numbers 1 to 376 represents the 5'-flanking region and the region of nucleotide numbers 3306 to 3528 represents the 3'-flanking region.

The transposon-like element Revolver-2 contains three exons and two introns. In SEQ ID NO:2 in the sequence listing, nucleotide numbers 377 to 504 represents the 5'-consensus region including a inverted repeat sequence (TGTCTACTACCGTCGCCCGGAAAAGAC: SEQ ID NO:18) and a subterminal repetitive sequence (TACCGTCGCC: SEQ ID NO:19) which are characteristic for the transposon terminals. The region of nucleotide numbers 505 to 846 represents the first exon region, the region of nucleotide numbers 847 to 1586 represents the first intron region, the region of nucleotide numbers 1587 to 1675 represents the second exon region, the region of nucleotide numbers 1676 to 2897 represents the second intron region, and the region of nucleotide numbers 2898 to 3208 represents the third exon region. The region of nucleotide numbers 3209 to 3305 represents the 3'-consensus region including a inverted repeat sequence (GTCCCATCCTGGGCATTACA: SEQ ID NO:20) and a subterminal repetitive sequence (ATCATTCTGGGA: SEQ ID NO:21) which are characteristic for transposon terminals.

DNA fragments comprising DNA sequence of the above-mentioned transposon-like element Revolver or Revolver-2 or a part thereof are useful as probes or markers to detect the genome of a useful resource plant. Here, the DNA fragments comprising DNA sequence of the above-mentioned transposon-like element Revolver or a part thereof mean DNA fragments which constitute a part of the nucleotide sequence according to SEQ ID NO:1 in the sequence listing. Also the DNA fragments comprising DNA sequence of the above-mentioned transposon-like element Revolver 2 or a part thereof mean DNA fragments which constitute a part of the nucleotide sequence according to SEQ ID NO:2 in the sequence listing.

Herein the term "useful resource plant" means plants having similarity and their genetic resources are useful. And, the plants included in that category are mainly Poaceae plants, and more specifically such plants are wheat, barley, rye, triticale and the like. Because homologs of Revolver may present in these Poaceae plants, it is believed that Revolver can be applied for development of gene markers.

Herein, "a DNA fragment comprising a part thereof" is not particularly limited, and means the DNA fragment corresponding to the part comprising 10 or more nucleotides, more preferably 20 or more nucleotides, and still preferably 50 or more nucleotides of the nucleotide sequence described in the sequence listing.

Using a probe or a primer obtained from this transposon-like element or transposon-like element containing regulatory element, it is possible to obtain other structural mutants of Revolver. In the following examples, by performing PCR using the sequence of the nucleotide numbers 3456 to 3478 which is the 3'-flanking region of SEQ ID NO:2 in the sequence listing as the primer, the present inventors obtained Revolver-3 (pSc626), Revolver-4 (pSc627), Revolver-5 (pSc628) and Revolver-6 (pSc5R1) which are Revolver non-autonomous elements. The 3'-flanking region of Revolver-2 (nucleotide numbers 3306 to 3527 of SEQ ID NO:2 in the sequence listing) and that of the above-mentioned non-autonomous elements are in common. The schematic figure of structures of these non-autonomous elements are shown in FIG. 1.

These non-autonomous elements have the nucleotide sequences in which 5'-upstream region of the second exon in the structure of Revolver or Revolver-2 is disrupted, and thus, they lack the first exon region. Therefore, Revolver-3, Revolver-4, Revolver-5 and Revolver-6 do not express mRNA of transposase, different from Revolver or Revolver-2, thus they are non-autonomous elements which is not transposable by themselves.

Revolver-3 (pSc626) of the present invention comprises the nucleotide sequence represented by nucleotide numbers 43 to 4311 shown in SEQ ID NO:3 in the sequence listing, is an non-autonomous element comprising 4269 nucleotide pairs, which has been mapped on the 6R chromosome. In SEQ ID NO:3 of the sequence listing, the region of nucleotide numbers 1 to 42 represents the 5'-flanking region, the region of nucleotide numbers 43 to 191 represents the 5'-consensus region including a inverted repeat sequence and a subterminal repetitive sequence which are characteristic for the transposon terminals, the region of nucleotide numbers 2598 to 2687 represents the second exon region, the region of nucleotide numbers 2588 to 3923 represents the second intron region, the region of nucleotide numbers 3924 to 4218 represents the third exon region, the region of nucleotide numbers 4219 to 4311 represents the 3'-consensus region including the inverted repeat sequence and the subterminal repetitive sequence which are characteristic for the transposon terminals, and the region of nucleotide numbers 4312 to 4479 represents the 3'-flanking region.

Revolver-4 (pSc627) of the present invention comprises the nucleotide sequence represented by nucleotide numbers 24 to 3242 shown in SEQ ID NO:4 in the sequence listing, and it is a non-autonomous element comprising 3219 nucleotide pairs. In SEQ ID NO:4 of the sequence listing, the region of nucleotide numbers 1 to 23 represents the 5'-flanking region, the region of nucleotide numbers 1567 to 1657 represents the second exon region, the region of nucleotide numbers 1658 to 2858 represents the second intron region, the region of nucleotide numbers 2859 to 3143 represents the third exon region, the region of nucleotide numbers 3144 to 3242 represents the 3'-consensus region including the inverted repeat sequence and the subterminal repetitive sequence which are characteristic for the transposon terminals, and the region of nucleotide numbers 3243 to 3413 represents the 3'-flanking region.

Revolver-5 (pSc628) of the present invention comprises the nucleotide sequence represented by nucleotide numbers 24 to 2688 shown in SEQ ID NO:5 in the sequence listing, is a non-autonomous element comprising 2665 nucleotide pairs, and it is mapped on 1R chromosome. In SEQ ID NO:5 of the sequence listing, the region of nucleotide numbers 1 to 23 represents the 5'-flanking region, the region of nucleotide numbers 1010 to 1095 represents the second exon region, the region of nucleotide numbers 1096 to 2288 represents the second intron region, the region of nucleotide numbers 2289 to 2589 represents the third exon region, the region of nucleotide numbers 2590 to 2688 represents the 3'-consensus region including the inverted repeat sequence characteristic for the transposon terminalsand the region of nucleotide numbers 2590 to 2688 represents the 3'-flanking region.

Revolver-6 (pSc5R1) of the present invention comprises the nucleotide sequence represented by nucleotide numbers 24 to 3526 shown in SEQ ID NO:6 in the sequence listing, is a non-autonomous element comprising 3503 nucleotide pairs, and it was mapped on 5R chromosome. In SEQ ID NO:6 of the sequence listing, the region of nucleotide numbers 1 to 23 represents the 5'-flanking region, the region of nucleotide numbers 2232 to 3146 represents the second intron region, the region of nucleotide numbers 3147 to 3426 represents the third exon region, the region of nucleotide numbers 3427 to 3526 represents the 3'-consensus region including the inverted repeat sequence characteristic the transposon terminals, and the region of nucleotide numbers 3527 to 3697 represents the 3'-flanking region.

The markers for location of the chromosome or the genome can be produced by making sequence tagged site (STS) from those obtained from Revolver or Revolver-2 as a probe. Moreover, because the above-mentioned non-autonomous elements have been already converted to STS, it is believed that they can provide other markers. The nucleotide sequences of both terminals of the fragments obtained by Revolver probe or primers can be determined, and then PCR primes can be designed based on the flanking sequences of Revolver. Then the region can be specifically amplified by PCR method to produce a sequence tagged site (STS) marker. It is believed that this chromosomal marker of Revolver which is a STS marker, is particularly useful as a marker for location of a chromosome or a genome.

Figure 2:
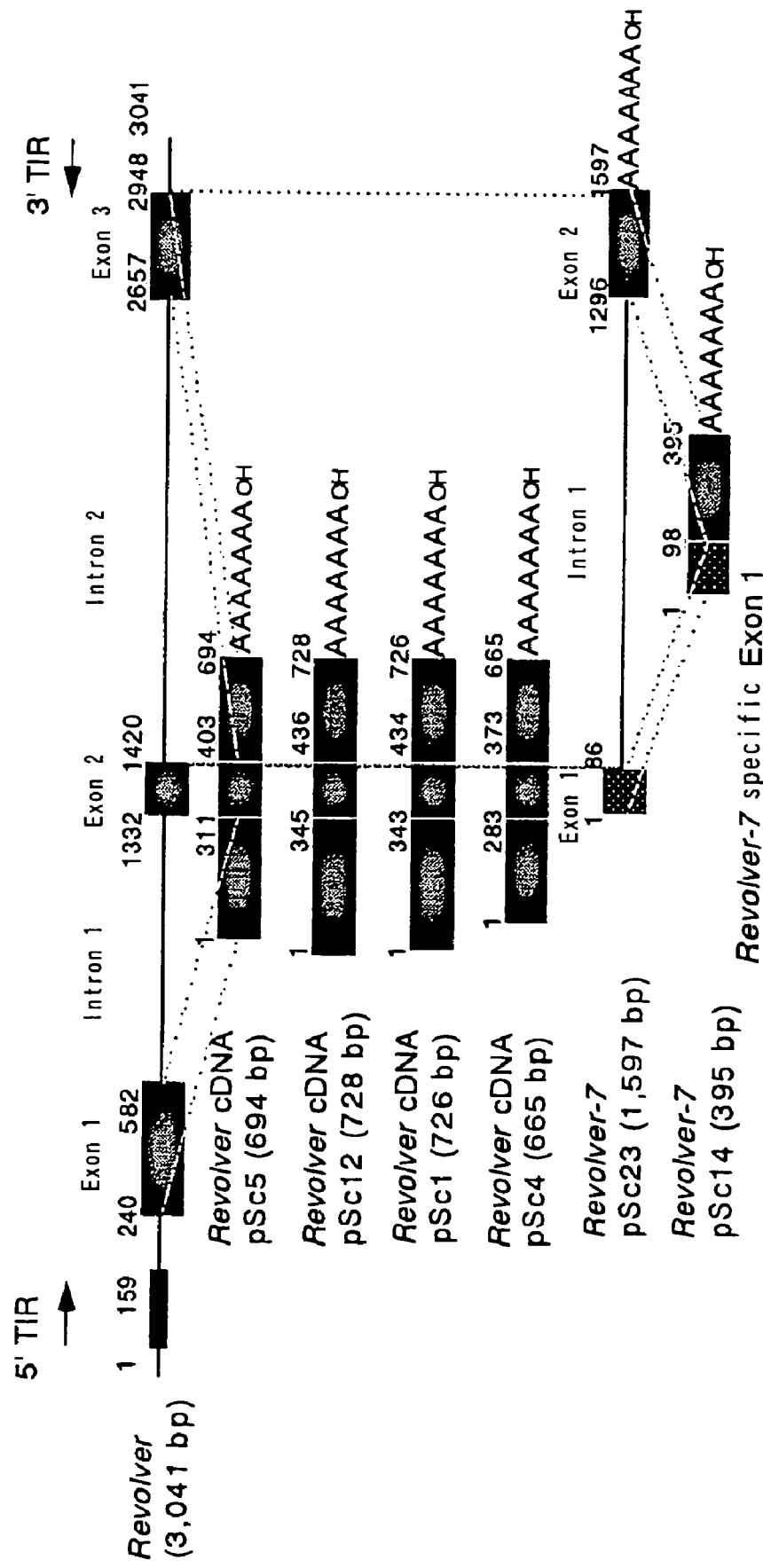
FIG. 2 is a schematic view showing structures of Revolver and cDNAs thereof.

Also, the present inventor has obtained 4 types of cDNA clones comprising the first, the second and the third exon of Revolver. The pSc1 comprising the nucleotide sequence represented by nucleotide numbers 1 to 726 in SEQ ID NO:8 in the sequence listing is such a cDNA clone of Revolver. In SEQ ID NO:8 in the sequence listing, the region of nucleotide numbers 1 to 342 represents the first exon region, the region of nucleotide numbers 343 to 433 represents the second exon region, and the region of nucleotide numbers 434 to 726 represents the third exon region. And by performing RT-PCR using both terminal regions as the primers, pSc5, pSc12 and pSc4 were obtained as other cDNAs. Relationships between the structure of Revolver and the respective cDNAs are shown in FIG. 2.

When the structures of these cDNAs are compared with that of pSc1, it has been shown that homology of the first exon is low but homology is high in the second and third exons. Such a cDNA of Revolver is pSc5 comprising the nucleotide sequence represented by nucleotide numbers 1 to 694 shown in SEQ ID NO:7 in the sequence listing. In SEQ ID NO:7 in the sequence listing, the region of nucleotide numbers 1 to 310 represents the first exon region, the region of nucleotide numbers 311 to 402 represents the second exon region, and the region of nucleotide numbers 403 to 694 represents the third exon region. The region of nucleotide numbers 110 to 463 represents coding region of transposase.

Also, such a cDNA of is pSc12 comprising the nucleotide sequence represented by nucleotide numbers 1 to 728 shown in SEQ ID NO:9 in the sequence listing. In SEQ ID NO:9 in the sequence listing, the region of nucleotide numbers 1 to 344 represents the first exon region, the region of nucleotide numbers 345 to 435 represents the second exon region, and the region of nucleotide numbers 436 to 728 represents the third exon region.

Also, such a cDNA of is pSc4 comprising nucleotide sequence represented by nucleotide numbers 1 to 665 shown in SEQ ID NO:10 in the sequence listing. In SEQ ID NO:10 in the sequence listing, the region of nucleotide numbers 1 to 282 represents the first exon region, the region of nucleotide numbers 283 to 372 represents the second exon region, and the region of nucleotide numbers 373 to 665 represents the third exon region.

It is believed that these cDNAs encode transposase of Revolver. Thus, by using these cDNAs, it enables transformation of Revolver across species of organisms and Revolver became transposable and transferable. Transformation and activation of Revolver can be applied for cloning by gene disruption and development of gene marker in various organisms. Methods of performing such transformation are widely known in the art.

Furthermore, the other type of cDNA clones have been also obtained The cDNA clones have the second intron and the third exon identical to Revolver, but the structure of the first exon is different. Such a cDNA of Revolver is pSc23 comprising the nucleotide sequence represented by nucleotide numbers 1 to 1597 shown in SEQ ID NO:12 in the sequence listing. In SEQ ID NO:12 in the sequence listing, the region of nucleotide numbers 1 to 86 represents the first exon region, the region of nucleotide numbers 87 to 1393 represents the second exon region, and the region of nucleotide numbers 1394 to 1597 represents the third exon region.

Furthermore, a cDNA clone which lacks the intron of pSc23 has been also obtained. Such a cDNA of Revolver is pSc14 comprising the nucleotide sequence represented by nucleotide numbers 1 to 395 shown in SEQ ID NO:11 in the sequence listing. In SEQ ID NO:11 in the sequence listing, the region of nucleotide numbers 1 to 98 represents the first exon region, and the region of the nucleotide numbers 99 to 395 represents the second exon region.

The transposase encoded by the cDNA of pSc1 is the protein comprising the amino acid sequence represented by amino acid numbers 1 to 117 shown in SEQ ID NO:13 in the sequence listing. Mutant proteins having 60% or more, preferably 70% or more, more preferably 80% or more, still preferably 90% or more and still more preferably 95% or more homology to the amino acid sequence represented by SEQ ID NO:13 in the sequence listing are also within the scope of the present invention so long as they have the characteristics as the transposase according to this invention.

EXAMPLES

Example 1

Structure of Transposon-Like Element Revolver (Cloning of Genome-Specific Repetitive Sequence by Subtraction Methods)

A genetic element, which is not present in wheat genome but is abundant specifically in rye genome, was cloned. Chromosomal DNA of rye was digested with restriction enzyme MboI which recognizes four nucleotides and genomic DNA of the wheat was randomly cleaved by sonication, then it was excessively mixed with the digested products. Double strand nucleotides bound by hydrogen bonds between complementary nucleotides were denatured at high temperature into single strand, and reproduced as the double strand DNA at room temperature. In the process of forming the double strands, the rye MboI fragments having common sequence with wheat DNA are associated with excessive wheat fragments of different lengths and different terminal forms, whereas MboI fragments with repetitive sequence specific for rye are re-associated one another to restore the double strands with cohesive ends. When plasmids with cohesive ends which is complementary to these restored DNAs are prepared as vectors, only double strands with cohesive ends specific for rye are ligated. By introducing this vector into *Escherichia coli* JM109, a DNA library in which the sequences common to wheat sequence are subtracted (deleted) from the rye DNA was constructed.

Genomic DNA was extracted according to Tomita's (1995) method. Matured leaves existing at the first and the second top of the plant body were collected before spike emergence, and stored in freeze at −80° C. This was frozen in liquid nitrogen, and then crashed. DNA extraction solution (2% CTAB, 100 mM Tris-HCl, 20 mM EDTA2Na, 1.4 M NaCl, pH 8.0) was added to it at the weight equivalent to the leaf powder, then incubated at 55° C. for one and a half hours or longer with stirring. This solution was extracted twice with chloroform/isoamyl alcohol (24:1). A ⅒ volume of sodium acetate (3 M) (pH 5.2) was added to the supernatant, and subsequently twice volume of 99.5% isopropanol was added at −20° C. to spool out polymerized and precipitated high molecular DNA. The spooled out DNA was dissolved in 5 ml of high salt TE (1 M NaCl, 10 mM Tris-HCl, 1 mM EDTA2Na, pH 8.0) followed by ethanol precipitation, and it was dissolved in 5 ml of TE (10 mM Tris-HCl, 1 mM EDTA2Na, pH 8.0). A 1/100 amount of RNase solution (1 mg/ml) was added to it, and incubated at 37° C. overnight. The presence or absence of RNA degradation and physical cleavage of DNA was confirmed by electrophoresis on 1% agarose gel. This DNA solution was extracted once with phenol/chloroform and chloroform respectively, then it was subjected to ethanol precipitation and dissolved in 5 ml of TE (10 mM Tris-HCl, 1 mM EDTA2Na, pH 8.0).

Genomic DNA was extracted by CTAB method (Murray & Thompson, 1980) from Chinese spring (CS, 2n=42) and chromosomal addition wheat Chinese spring lines (5R add CS, 6R add CS; 2n=44). The Chinese spring is a cultivar of common wheat (*Triticum aestivum* L.) and the Chinese spring addition lines are added with 5R or 6R chromosome from self-fertile rye (*Secale cereale* L.) line IR130. Evidence has been suggested that repetitive sequences of wheat species have been intricately differentiated by combining units of different repetitive sequences (Flavell & Smith, 1976; Smith & Flavell, 1977; Bedbrook et al., 1980; Flavell et al., 1981; McIntyre et al, 1988). Thus, in order to anneal the minimum unit in the repetitive sequence, the genomic DNA was digested into 2 kb or less using restriction enzyme MboI which recognized four nucleotides.

DNA of 6R add CS was digested with restriction enzyme MboI, separated on 0.8 to 1.0% agarose gel, and 0.5 to 2.0 kb fragments were recovered by liquid nitrogen freezing method (Koenen, 1989). The recovered DNA (6.6 μg) was mixed with DNA of CS cleaved into 1 kb or less by sonication, and this was placed in boiled water for 10 min to denature into single strands. To facilitate annealing of the DNA, the mixed DNA denatured into single strands was annealed in 4 ml of phenol emulsion buffer (0.8% phenol, 1.25 M sodium perchlorate, 0.12 M sodium phosphate, pH 6.8) for 72 hours.

Phenol emulsion was induced by rotating with a rotary evaporator. At that time, the types of the double strand DNA generated by annealing fragments of the restriction enzyme are composed of; those formed by association of the same restriction enzyme fragments to restore, those formed by association of fragments from different restriction enzyme, and those formed by association of excess amount of sonicated fragments. Among these, only double strand fragments in which the restriction enzyme fragments are restored have cohesive ends, and thus these fragments can be ligated to the vector. Such a DNA solution reconstructed by annealing was passed through Sephadex G-25 to eliminate phosphate salt. Subsequently, 3.2 μg of the DNA was used to ligate with BamHI site of pUC19, and competent *E. coli* JM109 strain by 0.1 M $CaCl_2$ and PEG 600 was transformed.

Recombinant plasmid was isolated by alkali SDS method (Brinboin & Doly, 1979) or by single step method (He et al., 1989), then an aliquot of 1 μg was spotted on two sheets of nylon membranes, and baked at 80° C. for 3 hours. Dot blot hybridization was performed for 14 hours using each of total DNA of rye IR130 (5 ng) or total DNA of wheat Chinese spring (10 ng) as a probe for one sheet of this nylon membrane, and clones with repetitive sequence exhibiting strong hybrid signals only for rye total DNA were selected. The probes were labeled by a random primer method using digoxigenin-11-dUTP (Boehringer Mannheim). In the method used to detect the probes, digoxigenin antibody labeled with alkali phosphatase (Boehringer Mannheim) was bound and color development of NBT or light generation of AMPPD was performed.

The MboI digested DNA fragments (13.4 μg), from chromosomal addition wheat line (2n=44) added with 5R of self-fertile rye line IR130, were mixed with 67.0 μg of CS (2n=42) DNA to denature into single strands, subsequently it was annealed in phenol emulsion and salted out by Sephadex G-25, which was used for cloning. The other methods were performed according to the above methods.

As the control of the above subtraction method, MboI fragments of self-fertile rye line IR130 was cloned into BamHI site of pUC19 by shot gun method.

As a result, 77 recombinant clones were obtained from 6R add CS by using 0.8 μg of DNA which were recovered from annealing procedure. The MboI fragments and the sonicated fragments were mixed at the ratio of 1:3, and thus 0.2 μg of the MboI fragment of 6R add CS was assumed to be contained in the DNA solution after annealing. Therefore, it is estimated that 385 recombinant clones were obtained per 1 μg of the MboI fragments. When 1 μg of the same MboI fragments were ligated to BamHI site of pUC19 by shot gun method without the above-mentioned preparation, $3.28 \times 10^4$ recombinant clones were yielded. The number of clones yielded after the annealing corresponded to 1.2% when compared with the number of the clones yielded by the shot gun method.

Thus, it appeared that 98.8% of the MboI fragments were randomly annealed with the sonicated fragments, whereas 1.2% of the MboI fragments were restored to be ligated to the vector. Hereinafter, the percentage for the number of the clones yielded by the shot gun method was considered to the restoration rate of the MboI fragments after the annealing. When 77 recombinant clones were dot-hybridized with total DNA of rye and wheat, 6 clones exhibited strong signals for rye genome.

The MboI fragments of 5R add CS were mixed with 67.0 μg of sonicated fragments of CS, subsequently annealed and desalted, then 20.0 μg was collected. From it, 500 ng was ligated to 20 ng of pUC19 to yield 145 recombinant clones. This means that 145 recombinant clones were yielded from 83.3 ng of Mob fragments of 5R and CS, and 1740 clones are yielded per 1 μg. The percentage for the yield of the shot gun method, i.e., the restoration rate of the MboI fragments by the annealing was 0.13%. When dot-hybridization was performed with total DNA of rye and wheat, 8 of 145 clones exhibited strong hybrid signals only for rye, which appeared to be the repetitive sequences specific for rye genome. Additionally, 5 clones exhibited hybridization with both rye and wheat, and 12 clones hybridized with only wheat genome.

As described above, a library including DNA fragments specific for rye genome was produced by subtracting wheat genomic DNA from genomic DNA of the rye chromosomal addition wheat line. From the restoration rate of the restriction enzyme fragments, it appeared that annealing of the mixture at a ratio of 1:5 (the restriction enzyme fragments: the sonicated fragments) resulted in this success. The insertion size of the repetitive clone was around 500 bp for the 6R add CS library, and 100 to 200 bp for the 5R add CS library.

From the DNA library obtained from the above-mentioned subtraction method, the nucleotide sequences were determined on 14 clones exhibiting strong and specific hybridization with the rye total genomic DNA. As a result, in three types of repetitive sequence known so far for rye, the sequences of 12 clones were homologous to two types of the known repetitive sequence (350 bp family: Bedbrook et al., 1980; R173 family: Rogowsky et al., 1992), however, two clones had unknown sequences which could not be found in databases of DNA nucleotide sequences. Hereinafter, out of the fragments, 89 bp fragment was used as a starting material, and the entire structure of the sequence was analyzed.

(Consensus Sequence of Transposon-Like Element Scattered in the Genome)

To clarify the entire structure of the 89 bp fragment, a library of large sized rye genomic DNA fragments was prepared, plural DNA fragments including the 89 bp fragment were selected from them, and the consensus sequences repeated in the genome were determined.

Genomic DNA of self-fertilie rye line IR27 was partially digested into sizes of 9 to 20 bp with restriction enzyme MboI, and the digested fragments were ligated to XhoI site of EMBL phage λ Fix IIDNA. These phage DNA were incorporated into phage particles, and then used to infect host E. coli, XL1-Blue MRA(P2) strain to prepare libraries of rye genomic DNA fragments. To select phages containing the 89 bp fragment from the genomic DNA libraries, infection was performed to form 50,000 plaques (bacteriolytic plaques) per plate of φ14 cm, due to the infection with the phages. Plaque hybridization was performed by transferring the plaques on this plate to a nylon membrane using the 89 bp fragment as a probe.

As a result, out of about 50,000 phage plaques, the 89 bp fragment hybridized with about 800 phage plaques. Therefore, it is estimated that the copy number of the 89 bp fragment in the rye genome is the number of the 89 bp fragment existing per 1 bp, that is[the number of positive plaque (800)/the average insertion length of rye genomic DNA libraries (13 kb)×the number of plaques screened (about 50,000)]×[the amount of chromosomal DNA per rye cell (7.8 Gb)]=1000.

Six phages hybridized with the 89 bp fragment were randomly selected, and restriction enzyme map of the rye DNA fragment inserted into phage was prepared for the purpose to determine the region in which the 89 bp fragment was included and the region to be used for nucleotide sequence determination. First, the rye DNA fragment ligated to the phage was cut off with T3 and T7 regions at both terminals by restriction enzyme NotI, and this was partially digested using 2 units of the restriction enzyme BamHI or SacI per 1 µg DNA with altering the reaction time from 2 min to 3 hours. After electrophoresis, this was transferred onto a nylon membrane, and then it was hybridized with T3 or T7 probe that labels both terminals to determine location relationship of respective restriction fragments. The DNA fragment inserted into the phage was completely digested with BamHI or SacI, and the hybridization was performed using the 89 bp fragment as a probe, and restriction fragments including the 89 bp fragment were determined.

In order to determine the nucleotide sequences of λ2, λ6 and λ8 in which the 89 bp fragment was located near the center of the restriction enzyme map, the inventors performed subcloning. The DNA fragments that hybridized with the 89 bp fragment and the DNA fragments flanking to it were harvested from agarose gel, and subcloned into the plasmid, pUC119 or pBlue ScriptII. The size which can be determined in one sequencing operation is about 70 bp, and thus for subclones longer than it, deletion clones were produced by deleting various lengths with exonuclease III or AluI, HaeI or AfaI, and they were subjected to dideoxy chain terminator reaction.

The inserted fragment of λ2 was cut into 8 DNA fragments with BamHI, and among these fragments, 7 fragments of 12.7 kb were subcloned. For four subclones, 58 deletion clones were produced in total by deleting nucleotides from both directions with approximately every 300 bp. The inserted fragment of λ6 was cut into 7 DNA fragments with SacI, and among these fragments, 3 fragments of 7.6 kb were subcloned. Furthermore, 45 deletion clones were produced from these three clones. The inserted fragment of λ8 was cut into 9 DNA fragments with SacI, and among these fragments, one fragment of 1.3 kb was subcloned, and 11 deletion clones were produced.

Figure 3:
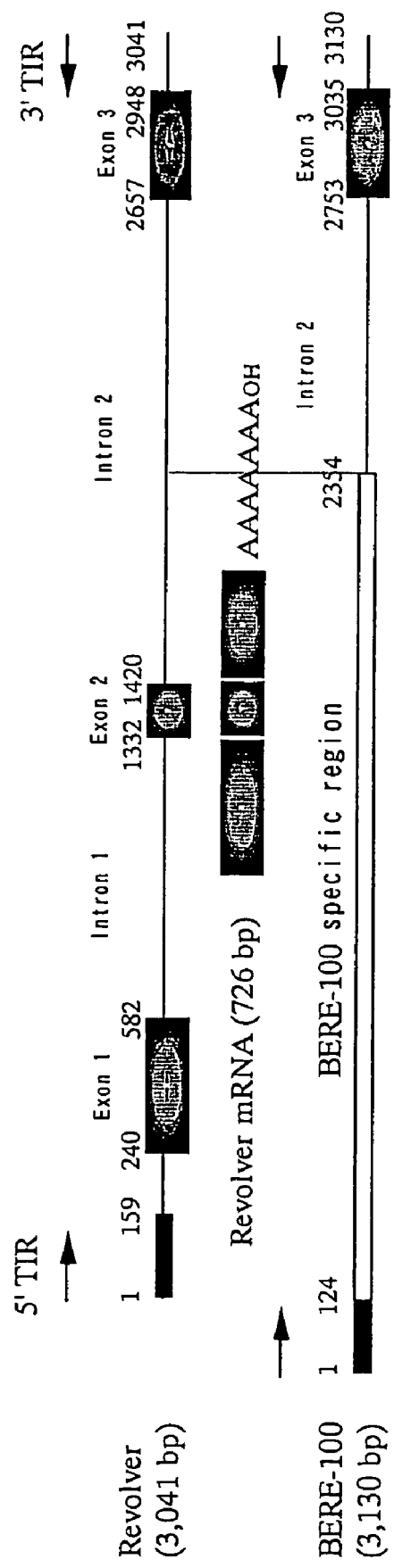
FIG. 3 is a schematic view showing the structure of Revolver compared in comparison with that of BARE-1.

With respect to the above-mentioned region of 21.6 kb, dideoxy chain terminator reaction was performed by cycle method using total of 117 plasmid clones as templates. The nucleotides which served as a terminal element was sequentially determined by DNA automatic sequencer. As a result, λ2 and λ6 were revealed to be transposon-like elements including consensus sequence of 3041 bp with 91.5% homology, having terminal inverted repeat sequences (TIR) of 20 bp at the terminals. This was named Revolver. The nucleotide sequence of Revolver is shown in SEQ ID NO:1 in the sequence listing. The structure of Revolver is shown in FIG. 3, in comparing with BARE-100.

The both terminal regions of Revolver (3,041 bp) was found as an insertion sequence in copia type retrotransposon BARE-1 of barley (Manninen & Schulman, 1993), and it has no analogous sequence except that they exhibit homology with both terminal regions of BARE-100 (3,130 bp) which is regarded as solo-LTR of gypsy type retrotransposon. A 149 bp region homologous (62% homology) to 5' terminal of BARE-100 exists upstream of transcription initiation site at 5'-side of Revolver. At the 3'-side of Revolver, the region of 768 bp ranging from middle of the second intron to 3'-terminal untranslated region existing downstream of the third exon, exhibits 62% homology to the 777 bp at 3'-side of BARE-100.

Revolver is a transposon-like inserted element sandwiched by the inverted repeat sequences at both terminals and scattered in the genome, and about 10,000 copies are scattered in the rye genome.

(Transcriptional Product of the Transposon-Like Element)

Total RNA was extracted from rye *Secale cereale* allogamous strains Petkus, *Triticum aestivum* cultivar Chinese spring, cultivar Gabo, rye 1R chromosome translocation type wheat Gabo line, and triticale. Mature leaves of the plant materials were stored at −80° C., and 1.0 g thereof was frozen in liquid nitrogen and crashed by homogenizer. A denaturing solution (4.2 M guanidine thiocyanate, 25 mM sodium citrate-2 hydrate, 0.5% sodium N-lauryl sarcosine) was added to this frozen powder and mixed by a vortex mixer to denature proteins.

A $\frac{1}{10}$ volume (1 ml) of 2M Sodium acetate (pH 4.0) was added thereto, then mixed upside down and an equivalent volume (1:1) of acid phenol (10 ml) was added and mixed. Furthermore, a $\frac{1}{5}$ volume (2 ml) of chloroform/isoamyl alcohol (49:1) was added at and mixed thoroughly upside down. After centrifugation for protein removal, the upper layer was collected. The denaturing solution (0.5 ml) was added to the isopropanol precipitated RNA pellet, and it was completely dissolved in a water bath of 45° C. Isopropanol (0.6 ml) was added and centrifuged to obtain RNA pellet. The supernatant was removed, 300 µl of DEPC treated water was added to the RNA pellet, and dissolved in the water bath of 45° C., and stored at −80° C.

Total RNA (5 µg) extracted from rye *Secale cereale* allogamous line Petkus, *Triticum aestivum* cultivar Chinese spring, cultivar Gabo, rye 1R chromosome translocation type wheat Gabo line and triticale were subjected to electrophoresis on 1% agarose gel at 20 V for 20 hours. Subsequently, RNA was transferred on a nylon membrane using vacuum blotting apparatus. The gel was placed on the blotting apparatus and 20×SSC was vacuumed by a vacuum pump for 2 hours. After the transfer, the nylon membrane was washed with 10×SSC, and DNA was cross-linked by UV (125 mJoule).

The transferred nylon membrane was immersed in a hybridization solution (2% blocking reagent (Boehringer Mannheim Biochemica), 5×SSC, 0.1% N-lauroyl sarcosine, 0.02% SDS), and prehybridization was performed for 4 hours. Next, hybridization was performed in 10 ml of the hybridization solution containing 200 ng of DNA fragment of labeled Revolver cDNA pSc1 (726 bp) at 65° C. for 20 hours. The membrane was washed twice with 2×SSC and 0.1% SDS at room temperature for 5 min, and twice with 0.1×SSC and 0.1% SDS at 65° C. for 15 min.

Furthermore, it was washed with a washing buffer (0.3% (w/v) Tween 20/buffer 1, buffer 1:0.1 M maleic acid, 0.15 M NaCl, pH 7.5) for 3 min, then it was blocked with blocking buffer 2 (1% (w/v) blocking reagent (Boehringer Mannheim Biochemica)/buffer 1) for 30 min, and antigen-antibody reaction was performed for 30 min in buffer 2 containing 0.01% anti-digoxigenin-AP, Fab fragments (750 units/ml). This was washed twice for 30 min with the washing buffer, incubated in buffer 3 (0.1 M Tris-HCl, pH 9.5, 0.1 M NaCl, 0.05 M MgCl$_2$) for 5 min, subsequently 2 ml of CDP Star solution (0.1% CDP/buffer 3) was dripped to enclose the nylon membrane in a Hybri Bag, then it was incubated at 37° C. for 10 min. Furthermore, the nylon membrane was contacted with X-ray film and exposed for 3 hours, then signals of the hybridization were detected. It was found that the transposon-like element Revolver was transcripted to RNAs of 0.4 kb, 0.7 kb, 3 kb and 5 kb.

From the total RNA of the self-fertile rye line IR10, mRNA was extracted by poly A tract mRNA isolation system (Promega), a single strand cDNA was synthesized by MMLV reverse transcriptase utilizing oligo d(T) with XhoI linker as a primer, and an EcoRI adaptor was added thereto. The cDNA was ligated to λ ZAPII DNA, phage particles were formed by in vitro packaging, and they were used to infect host bacteria XLI-Blue MRF' to prepare cDNA library of 1.4×10$^6$ pfu.

Using Revolver (clone λ2) as a probe, the cDNA library was hybridized with 250,000 plaques and 9 positive phages were selected and 3 phages were selected by the second screening. Furthermore, 3 positive phages were co-infected with helper phages to synthesize phagemid DNA, and the DNA nucleotide sequence was determined by cycle sequence method. Using such a procedure a cDNA clone pSc1 was obtained, and the nucleotide sequence is shown in SEQ ID NO:8 in the sequence listing. It has been found that Revolver comprises three exons (342 bp, 88 bp, 291 bp) and two introns (750 bp, 1237 bp) by structural comparison of the genomic DNA clone of the transposon-like element Revolver with pSc1.

And mRNA of Revolver underwent processing had one open reading frame encoding a polypeptide comprising 117 amino acid residues. The amino acid sequence of the polypeptide of transposase encoded by Revolver cDNA is shown in SEQ ID NO:13 in the sequence listing.

Example 2

Genes of Transposon-Like Element Revolver and Proteins Encoded by the Gene (Classification of Revolver mRNA of Ryes)

Total RNA was extracted from leaves of self-fertile rye line cultivar Secale cereale, S. fragile (wild species), S. silvestre, a rye chromosomal translocation wheat line), a rye chromosomal addition wheat line and a common wheat, and RT-PCR was performed using primers designed from both terminals of Revolver cDNA pSc1(726 bp). The reaction was performed with AMV reverse transcriptase using 38-mer oligo dT primer[726RT38 (5'-TTTTTTTTTTTTTTGGCACAACTCATG-TAAAAGAGGG-3': SEQ ID NO:22 (Tm value 74.6)) containing 23 nucleotides at the 3' terminal of the Revolver cDNA. RNA PCR kit (AMV) Ver. 1.1 (Takara) was used. A single strand cDNA was synthesized by reverse transcription reaction. Furthermore, using the reverse transcription product as a template, a double strand cDNA sandwiched by the 726RT38 primer of 38-mer and 726-5F primer of 22-mer (5'-GGCACGAGGGTACGAGTCCGAG-3': SEQ ID NO:23 (Tm value 73.0)) was amplified. A reaction solution (total volume 50 μl) containing 200 nM of the primers (33 ng), 100 μM of dNTPs, 50 mM of KCl, 10 mM of Tris-HCl (pH 8.8), 1.5 mM of MgCl$_2$ and 1U of Taq DNA polymerase was prepared using 20 ng of DNA as a template.

Using thermal cycler PC-700 (ASTEC), a series of PCR reaction consisting of denature at 95° C. for 30 sec, annealing at 63° C. for 30 sec and elongation at 72° C. for 1 min was performed 30 times. The first denature at 94° C. and the final synthesis at 72° C. were performed for 5 min, respectively. PCR products from rye, wheat CS and rye chromosomal addition wheat CS line series were subjected to electrophoresis on 1.5% agarose gel at 100 V for one and a half hours. As a result, cDNAs of about 0.7 kb and 1.5 kb were amplified significantly.

The PCR products were transferred onto a nylon membrane (BIODYNE PLUS) using a vacuum blotting apparatus. The gel was placed on the blotting apparatus, and 0.25 N HCl was poured on the gel while vacuuming for 3 min by a vacuum pump for depurination. Likewise, the gel was covered with 0.4 N NaOH and vacuumed for one hour. After completion of the transfer, the nylon membrane was washed with 2×SSC and subsequently the DNA was cross-linked by UV (125 mJoule). Also in the gel blotting of the RT-PCR products, cDNA probes derived from Revolver pSc1 was hybridized with the DNAs of 0.7 kb and 1.5 kb.

The cDNAs which exhibited homology in the gel blot hybridization with the RT-PCR product were cloned to pGEM-T vector, and the nucleotide sequences were determined by cycle sequence method.

As a result of analysis on 30 cDNA clones of Revolver obtained by TA cloning of the RT-PCR products, the total lengths of the products were 665 to 723 bp, and they were classified into three classes (I, II and III) having the first exon of different structures (homology in the class I: 89%, II: 97% and III: 93%). The cDNA clones thus obtained are pSc5 (class I) shown in SEQ ID NO:7 in the sequence listing, pSc12 (class II) shown in SEQ ID NO:9 in the sequence listing, and pSc4 (class III) shown in SEQ ID NO:10 in the sequence listing, and pSc1 is classified to the class II.

The homologies between the classes are: 75% for class I and class III, 80% for class I and class III, and 76% for class I and class III. According to comparison between the exons, the second exon (89 to 92 bp) and the third exon (293 bp) exhibited high homologies of 91 to 95% in the different classes. On the contrary, the first exon exhibited high homology in the classes (I: 98%, II: 99%, III: 99%), however, the homologies between different classes were low value of 60s % (63% between I and II, 64% between I and III, 67% between II and III). In the first exon, partial deletions and mutations of different lengths were found in the nucleotide sequences of the respective three classes. Thus, the classification of the cDNA corresponds to the structural mutations of the first exon. Moreover, many repetitive sequences of a same direction composed of units of 8 to 14 bp are present in the first exon and non-homologous recombination occurs between alleles, which caused various structural mutations. By the cDNA analysis of the transposon-like element Revolver, three sub-families were revealed to exist, wherein the regions of the second exon and the third exon are nearly identical while the region of the first exon is different due to partial duplication, deletion and etc.

As described above, diversities were found in the structures of the first exon of the Revolver gene, which has transcription activity and obtained from the self-fertile pure rye line, and it is remarkable as a landmark of the genome.

(Classification of Revolver mRNA in Plants of Wheat Species)

Mutation of Revolver mRNA was analyzed in wheat species *Triticeae*. Revolver cDNAs were obtained from mature leaves of *S. fragile, S. silvestre, T. monococcum, Ae. squarrosa*, and *D. villosum* by RT-PCR method and structures of the cDNAs were determined. Total RNA was extracted, and RT-PCR was performed using primers designed from both terminals of Revolver cDNA pSc1(726 bp). Single strand cDNA was synthesized with AMV reverse transcriptase using oligo dT primer of 38-mer[726RT38 (5'TTTTTTTTTTTTTTTGGCACAACTCATG-TAAAAGAGGG-3': SEQ ID NO:22 (Tm value 74.6)) containing 23 nucleotides at the 3' terminal of Revolver cDNA. RNA PCR kit (AMV) Ver. 1.1 (Takara) was used.

Furthermore, using the reverse transcription product as a template, double strand cDNA sandwiched by the 726RT38 primer of 38-mer and 726-5F primer of 22-mer (5'-GGCAC-GAGGGTACGAGTCCGAG-3': SEQ ID NO:23 (Tm value 73.0)) was amplified. A reaction solution with total volume of 50 μl containing 200 nM of primers (33 ng), 100 μM of dNTPs, 50 mM of KCl, 10 mM of Tris-HCl (pH 8.8), 1.5 mM of $MgCl_2$ and 1U of Taq DNA polymerase was prepared using 20 ng of DNA as a template. Using thermal cycler PC-700 (ASTEC), a series of the PCR reaction with denature at 95° C. for 30 sec, annealing at 63° C. for 30 sec and elongation at 72° C. for 1 min was performed 30 times. As a result, the majority belonged to class I (47%) or class II (27%) of *S. cereale*, and major two classes were conserved beyond the species. Therefore, existence of the three classes appeared not to be a creature of chance.

(Conservation of Revolver Coding Region Beyond Species)

Revolver produces mRNA of 0.7 kb vigorously, in which, the class I mRNA encodes ORF of 118 amino acid residues (SEQ ID NO:13 in the sequence listing) conserved in the wheat plants species beyond species.

Example 3

Emergence, Disappearance, and Structural Mutation of Transposon-Like Element Revolver (Emergence and Disappearance of Revolver in Poaceae Plants)

In order to examine distributions of Revolver in Poaceae plants, genomic DNAs were extracted from rye *Secale cereale* (RR) cultivar Petkus, self-fertile lines (IR-10, IR48-1), wild lines of rye genus (*S. montanum, S. fragile, S. silvestre*), wheat *Triticum aestivum* (AABBDD), *T. monococcum* (AA), *T. durum* (AABB), *T. polonicum* (AABB), *T. timopheevi* (AAGG), *T. tauschii* (DD), a rye chromosome translocation wheat line (DRA-1), a rye chromosomes (1R to 7R) addition wheat lines, *Dasypyrum villosum* (VV), barley *Hordeum bulbosum* (HH) and rice plant *Oryza sativa*. They were completely digested with restriction enzymes SacI and DraI.

The genomic DNA (each 20 μg)of these plants were subjected to electrophoresis on 1% agarose gel at 20 V for 20 hours. Subsequently, the DNA samples were transferred onto a nylon membrane (Biodyne Plus) using a vacuum blotting apparatus. The gel was placed on the blotting apparatus, and 0.25 N HCl was poured on the gel while vacuuming for 3 min by a vacuum pump for depurination. Subsequently, the gel was vacuumed with 0.4 N NaOH for 2 hours. After the transfer, the nylon membrane was washed with 5×SSC and the DNA was cross-linked by UV (125 mJoule).

The transferred nylon membrane was immersed in a hybridization solution (2% blocking reagent (Boehringer Mannheim Biochemica), 5×SSC, 0.1% N-lauroyl sarcosine, 0.02% SDS), and pre-hybridization was performed for 4 hours. Subsequently, hybridization was performed for 20 hours at 65° C. in 10 ml of hybridization solution containing 200 ng of labeled Revolver cDNA pSc1(726 bp) DNA fragment. The membrane was washed twice with 2×SSC and 0.1% SDS at room temperature for 5 min, and twice with 0.1×SSC and 0.1% SDS at 65° C. for 15 min.

Furthermore, it was washed with a washing buffer (0.3% (w/v) Tween 20/buffer 1, buffer 1:0.1 M maleic acid, 0.15 M NaCl, pH 7.5) for 3 min, then blocking was performed for 30 min with buffer 2 (1% (w/v) blocking reagent (Boehringer Mannheim Biochemica)/buffer 1), and antigen-antibody reaction was performed for 30 min in the buffer 2 containing ¹⁄₁₀₀₀ anti-digoxigenin-AP, Fab fragments (750 units/ml).

It was washed twice with the washing buffer for 30 min, incubated in buffer 3 (0.1 M Tris-HCl, pH 9.5, 0.1 M NaCl, 0.05 M $MgCl_2$) for 5 min, subsequently 2 ml of CDP Star solution (0.1% CDP/buffer 3=1:100) was dripped and the nylon membrane was enclosed in a Hybri Bag, then it was incubated at 37° C. for 10 min. Furthermore, the nylon membrane was contacted with an X-ray film and exposed for 1 to 3 hours, and hybridization signals were detected.

The cDNA probe (726 bp) hybridized strongly with DNAs from *Secale cereale, S. montanum, S. fragile, S. silvestre* and *Dasypyrum villosum* (VV) which were R genome species. Moreover it hybridized moderately with DNAs from *Triticum monococcum* (AA), *T. durum* (AABB), *T. polonicum* (AABB), *T. timopheevi* (AAGG) and *T. tauschii* (DD). It also hybridized with DNAs from *Hordeum bulbosum* (HH) and *Oryza sativa*, but not hybridized with DNA from *T. aestivum* (AABBDD).

From these findings, it was revealed that Revolver is present in RR genome, AA genome, AABB genome and DD genome but not in AABBDD genome of the common wheat. Interestingly, Revolver is not present in the common wheat, but is present in A genome and D genome which are closer to the ancestral species.

Figure 4:
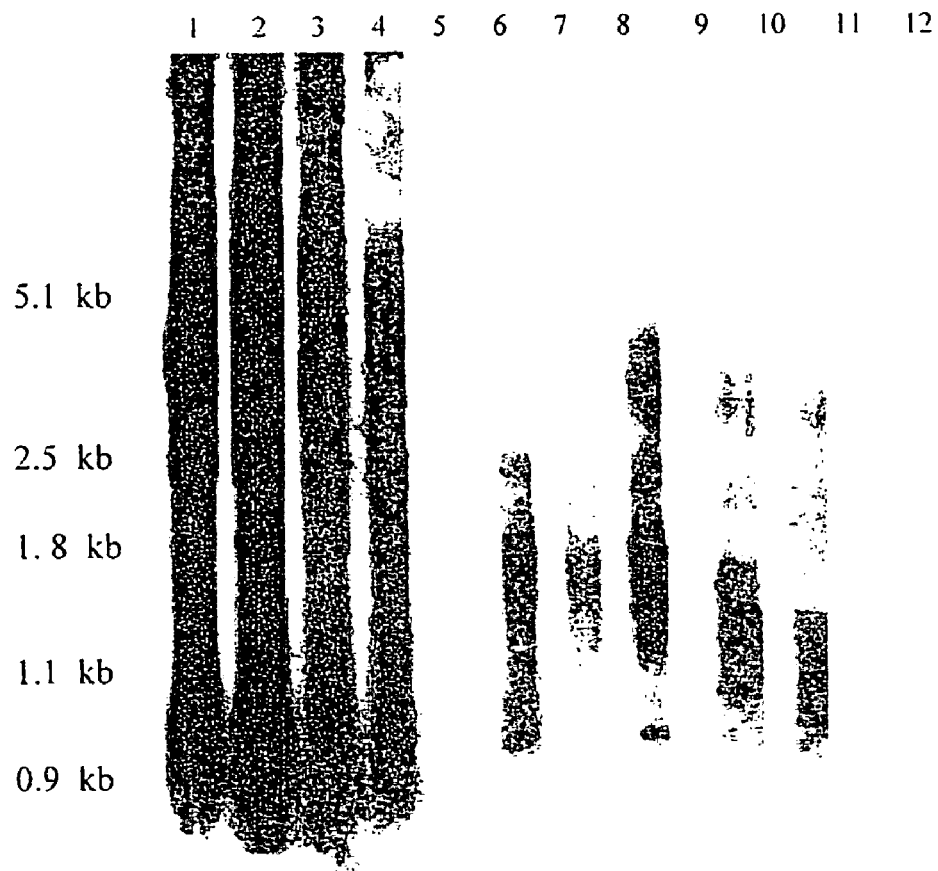
FIG. 4 is a photograph of Southern blotting analysis of Revolver in various species of wheat plants.

In Southern blot analysis of *Triticum* plants (FIG. 4), the cDNA probe of Revolver strongly hybridized with DNAs from three rye species of *S. cereale, S. fragile* and *S. silvestre*, and *Dasypyrum villosum*. Moreover, it moderately hybridized with *Triticum monococcum* and *Aegilops squarrosa*. Therefore, Revolver is present as many copies in *Secale* and *Dasypyrum* genus, in addition, Revolver is present with moderate repeats in diploid species such as *Triticum monococcum* and *Aegilops squarrosa* as well as tetraploid species such as *Triticum durum*, but it is not present in the common wheat. Revolver has been amplified in some related species in the process of evolution from ancestral species of wheat but it has disappeared in the common wheat. Thus, Revolver is useful as a genetic marker of the related species in wheat genome. As copy numbers of revolver are different among the wheat related plant species, it is attractive as an index of genomic evolution and a landmark of chromosomes.

(Structural Diversities in the Genome of Revolver)

PCR is performed using the 3'-flanking region GTAGTCGTCAGGAGTCCTCACCA (SEQ ID NO:24) derived from one clone of Revolver (Revolver-2; SEQ ID NO:2 in the sequence listing) as a single primer, and 4 types DNA (2.3 kb, 2.8 kb, 3.3 kb and 4.3 kb) are amplified from the rye genome, but nothing is amplified from the wheat genome. Genetic character of rye and that of wheat can be distinguished by this primer easily. Furthermore, when PCR is performed with the same primer using the genomic DNA from rye chromosomal addition wheat line as a template, DNAs of 2.8 kb, 3.6 kb and 4.3 kb are amplified from 1R, 5R and 6R chromosomal addition lines, respectively. By PCR with this primer, rye chromosomes 1R, 5R, 6R and 7R can be distinguished and identified. Each one DNA from the DNAs of chromosomal addition lines of 1R, 5R, 6R and 7R, four types of DNAs amplified from the rye genome, was cloned using pGEM-T vector, then the nucleotide sequences were determined. As a result, all of them were non-autonomous elements of Revolver which have the second intron of Revolver and the down-stream region thereof, but they have structural mutations occurred at the 5'-side.

First, Revolver-3 (SEQ ID NO:3 in the sequence listing) located on 6R chromosome comprises total length of 4269 bp, and at the 3'-side, it has the region of 2112 bp from the middle of the first intron of Revolver through the third exon and reaching to the 3' terminal. At the 5' side, it has the homologous region of 150 bp including the inverted repeat sequence. However, as to the region of about 2 kb between these sequences, it lacks the region from the first exon to the middle of the first intron, while it includes the region of 370 bp highly homologous to the insert sequence of BARE-100 (3130 bp) from barley which is not present in Revolver. Thus, its sequence is quite different from Revolver.

Both of Revolver-3 (pSc626) and BARE-100 include Revolver consensus sequence at the 5' terminals. At the 5' terminal, both include 14 bp of 5' terminal consensus sequence of gypsy type transposon LTR, and have the region of 123 to 149 bp homologous to upstream of the transcription initiation site of Revolver, and further the homologous region specific for Revolver-3 (pSc626) and BARE-100 continues until around 600 bp.

On the other hand, they include the region homologous to the transcribed region of Revolver at the 3' side, Revolver-3 (pSc626) has the region of 2,112 bp from the middle of the first intron to the downstream of the third exon, and BARE-100 has the region of 777 bp from the middle of the second intron to the downstream of the third exon. The both 3' terminals coincide with the 3' terminal of the untranslated region downstream of the third exon of Revolver and include the 14 bp 3'-terminal consensus sequence of gypsy type transposon LTR. Referring to the homology with Revolver of each region, in the region homologous to Revolver, Revolver-3 (pSc626) exhibited homology from 77 to 93%, and BARE-100 exhibited homology from 58 to 65%, and in the 5' terminal region homologous to only Revolver-3 (pSc626) and BARE-100, the homology was 65%.

In the region from 631 to 2,176 bp at the 5' side of Revolver-3 (pSc626) and the region from 598 to 2,353 bp of BARE-100, there exist short repetitive sequences occurring repeatedly and both clones exhibit 53% homology, but no homology was observed with Revolver. Revolver-3 (pSc626) and BARE-100 have unique consensus region at the 5' side, and they exhibited a high homology in total. BARE-100 corresponds to the type wherein the region from the first intron to the second intron is deleted from Revolver-3 (pSc626).

Next, the total length of Revolver-4 (pSc627) consists of 3,219 bp (SEQ ID NO:4), and at the 3' side, it has the region of 1806 bp ranging form immediately before the second exon to the 3' terminal of Revolver. However, in the 1,413 bp at the 5' side, the region homologous to Revolver is limited to only 101 bp at the 5' terminal.

Further, Revolver-5 (pSc628) located on 1R chromosome has total length of 2,665 bp (SEQ ID NO:5 in the sequence listing), and at the 3' side, it has the region of 1,826 bp ranging from immediately before the second exon to the 3' terminal of Revolver. At its 5' side, the region homologous to Revolver is limited to only 37 bp at the terminal region, but the region of about 670 bp is homologous to Revolver-4 (pSc627).

Finally, Revolver-6 (pSc5R1) (SEQ ID NO:6 in the sequence listing) amplified from 5R chromosome has total length of 3,503 bp, and at the 3' side it has the region of 1,294 bp ranging from the middle of the second intron to the 3' terminal of Revolver, however, at the 5' side there is not a region homologous to Revolver, and 121 bp at the 5' terminal is homologous to Revolver-4 (pSc627) and Revolver-5 (pSc628).

(Structural Diversities of Revolver mRNA)

In order to find characteristics and mutations of respective Revolver species, structural analysis of the cDNA clones was performed. As a result, cDNAs exhibiting completely different structures at the first exon were found. Five cDNAs cloned from *Secale silvestre*, a wild species of rye, have total length of 1,597 bp and contained the second intron (1,210 bp) and the third exon (301 bp) of Revolver, but at the 5' terminal they have the 86 bp sequence not observed in Revolver. The homology among the 5 clones were 96%. On the other hand, four cDNA clones cloned from rye cultivar species *S. cereale* have total length of 395 bp, and lack the second intron compared to the above cDNA clones of 1,597 bp. From the reason described above, an element having total length of 1,597 bp, the element consists of two exons and one intron, and contains specific first exon of 86 bp, and the structure downstream of the intron is common to Revolver, is shown to exist. This third type of Revolver family is named Revolver-7 (pSc23) (SEQ ID NO:12 in the sequence listing).

Meanwhile, another cDNA clone screened from a cDNA library of leaf(pSc14, total length of 2,182 bp) has the second exon (90 bp, homology 97%) and the third exon (260 bp, homology 92%) of Revolver, but the region corresponding to the first exon is extremely long and it has no homology with the other cDNA clones (SEQ ID NO:11). The members of Revolver family, having common structure of downstream of the second intron, are actively transcribed and various structural diversities are observed at the 5' side.

Example 4

Development of Chromosomal Markers by Transposon-Like Element Revolver (Identification of Chromosome by in Situ Hybridization of Revolver)

Chromosomal specimens at metaphase of somatic mitosis are produced for rye cultivar Petkus, and the 370 bp region specific for the 5' side of Revolver and BARE-100 was analyzed for its chromosomal location by FISH method. The total length of consensus sequence of 3,041 bp, contained in the clone Revolver-1, was labeled with biotin-16-dUTP to produce a probe of Revolver, and the region of 370 bp homologous to BARE-100 is used for a probe of Revolver-3 (pSc626) specific region. After the hybridization, the probe on the chromosome was detected by an indirect fluorescent method via avidin-FITC. The identification of the rye chromosome was performed by simultaneous FISH method with a tandem repetitive sequence family of 350 bp at the terminal region (labeled with dig, detected by rhodamine anti-dig antibody) or C-band method after the FISH.

The Revolver probe showed weak hybridization with the rye chromosomes entirely and relatively large signals scattered in dot shape were detected. The signals in dot shape were stably detected one position at the middle intervening region of the short arm on the 1R chromosome; two positions at the proximal terminal and the intervening region near the centromere of the short arm on the 2R chromosome; and one position at the middle intervening region of the short arm and two positions at the region near the centromere and the middle intervening region of the long arm on the 5R chromosome. Then 1R, 2R and 5R chromosomes can be definitely distinguished by the Revolver probe. On the other hand, the 370 bp region of Revolver-3 (pSc626) common to BARE-100 hybridized entirely with the rye chromosome rather strongly, and the region is scattered with copy numbers higher than Revolver.

(Chromosomal Markers by Making STS of Various Structural Mutants of Revolver)

Among the genomic clones of Revolver, clones assumed to be non-autonomous elements were selected, for the clones have the second intron of Revolver and the region downstream from it, but they received structural mutation at the 5' side. Such clones were made to STS on rye chromosome using the rye chromosome wheat line. Revolver-3 was made to STS on the 6R chromosome because it was amplified with the 3'-flanking region primer GTAGTCGTCAGGAGTCCT-CACCA (SEQ ID NO:24) of Revolver-2 only from the rye 6R chromosomal addition line.

Revolver-5 (pSc628) was located on the rye 1R chromosome because it was amplified with the 3'-flanking region primer, GTAGTCGTCAGGAGTCCTCACCA (SEQ ID NO:24) of Revolver-2 only from the rye 1R chromosomal addition line. Furthermore, Revolver-6 (pSc5R1) is located on the rye 5R chromosome because it was amplified with the 3'-flanking region primer, GTAGTCGTCAGGAGTCCT-CACCA (SEQ ID NO:24) of Revolver-2 only from the rye 5R chromosomal addition line.

Moreover, DNA consisting of 2,973 bp specific for the 5R chromosome is certainly amplified using the internal sequences of Revolver-6 (pSc5R1), ATAGCTCCACTGT-TGGCTCCTCTTDC (SEQ ID NO:25) and CATTCATC-CAAAGAACACAGAGTCCG (SEQ ID NO:26), as the primers. Revolver-2 was located on the rye 7R chromosome because DNA of 492 bp was amplified only from the rye 7R chromosomal addition line by PCR using the 5'-flanking region of Revolver-2 GCCTTTCGGCCTTCCTCTCAG-GCGG (SEQ ID NO:27) and GTACTTGGCATCGGTA-GATGTTCGG (SEQ ID NO:28). As the above, by the PCR primers comprising the sequences flanking to each element of Revolver scattering in the genome, internal sequences of such element or combination thereof, the chromosome on which each element of Revolver is located can be determined, and further such PCR primers can be utilized for detection and identification of the chromosome.

The first exon region of Revolver-7 comprises 98 bp in S. cereale (Revolver-7, pSc23) and 86 bp in S. silvestre (Revolver-7, pSc14). Thus, the sequence is designed to amplify the first exon region of Revolver-7 (pSc23), and PCR was performed for S. cereale, S, silvestre and Dasypyrum villosum, which contain many insert element families. As a result, the DNA corresponding to the first exon is amplified, and it consists of about 90 bp in S. silvestre and D. villosum, and it consists of about 100 bp in S. cereale. The insert elements are present in the genome entirely, therefore, the primer set of the first exon region of Revolver-7 is useful to distinguish and identify DNA of S. cereale and that of D. villosum utilizing the genetic background of the wheat.

INDUSTRIAL APPLICABILITY

The DNA sequence of the transposon-like element Revolver of the present invention, the DNA sequence of the gene with transcription activity encoded by Revolver and the DNA sequences of the structural mutants thereof can be utilized for detection, identification of the genome of useful resource plants, development of DNA markers, identification of chromosomes, probes for study on evolution, entry points of PCR, and the like.

What is claimed is:

1. An isolated nucleic acid comprising
   (a) a nucleotide sequence of positions 377 to 3,305 of SEQ ID NO:2, or
   (b) a nucleotide sequence having no less than 90% identity with the nucleotide sequence of part (a), and that hybridizes with the nucleotide sequence of part (a) under stringent conditions.

2. An isolated nucleic acid comprising
   (a) a nucleotide sequence of positions 1 to 3,528 of SEQ ID NO:2, or
   (b) a nucleotide sequence having no less than 90% identity with the nucleotide sequence of part (a), and that hybridizes with the nucleotide sequence of part (a) under stringent conditions.

3. A probe or a primer consisting essentially of a detectable label and a nucleic acid, wherein said nucleic acid is a fragment of the nucleic acid according to claim 1 and said fragment consists of 20 or more consecutive nucleotides of SEQ ID NO:2.

4. A probe or a primer consisting essentially of a detectable label and a nucleic acid, wherein said nucleic acid is a fragment of the nucleic acid according to claim 2 and said fragment consists of 20 or more consecutive nucleotides of SEQ ID NO:2.

5. A method for determining the presence or absence of elements of a rye genome in a plant comprising hybridizing to the probe or primer according to claim 3 or 4 to the genomic DNA of said plant; thereby determining that elements of a rye genome are present in said plant.

6. A method for identifying a chromosome of a plant comprising elements of a rye genome; said method comprising the step of hybridizing the probe or primer of claim 3 or 4 with the chromosome of the plant; thereby identifying a chromosome comprising elements of a rye genome.

7. An isolated nucleic acid consisting of 20 or more consecutive nucleotides of SEQ ID NO: 2.

8. An isolated nucleic acid consisting of 50 or more consecutive nucleotides of SEQ ID NO: 2.

* * * * *